US007390806B2

(12) United States Patent
Lee et al.

(10) Patent No.: US 7,390,806 B2
(45) Date of Patent: Jun. 24, 2008

(54) ANTIBIOTICS CONTAINING BORINIC ACID COMPLEXES AND METHODS OF USE

(75) Inventors: Ving Lee, Los Altos, CA (US); Stephen J. Benkovic, State College, PA (US); Stephen J. Baker, Mountain View, CA (US); Kirk R. Maples, San Jose, CA (US); Tsutomu Akama, Sunnyvale, CA (US); Yong-Kang Zhang, San Jose, CA (US); Rajeshwar Singh, Edmonton (CA); Vittorio A. Sauro, Edmonton (CA); Chetan Pandit, Edmonton (CA); Zhuoyi Su, Edmonton (CA); Zhixiang Yang, Edmonton (CA)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 122 days.

(21) Appl. No.: 10/867,465

(22) Filed: Jun. 14, 2004

(65) Prior Publication Data

US 2005/0070503 A1 Mar. 31, 2005

Related U.S. Application Data

(63) Continuation-in-part of application No. 10/740,304, filed on Dec. 18, 2003.

(60) Provisional application No. 60/434,375, filed on Dec. 18, 2002, provisional application No. 60/436,095, filed on Dec. 23, 2002, provisional application No. 60/437,849, filed on Jan. 3, 2003.

(51) Int. Cl.
*C07D 484/04* (2006.01)
*C07D 215/02* (2006.01)
*C07D 215/20* (2006.01)
*C07D 239/70* (2006.01)
*C07D 253/08* (2006.01)
*A61K 31/47* (2006.01)
*A61P 31/04* (2006.01)
*A61P 31/10* (2006.01)

(52) U.S. Cl. .................. 514/242; 514/248; 544/69; 546/13

(58) Field of Classification Search ............... 544/69; 546/13; 514/242, 248
See application file for complete search history.

(56) References Cited

U.S. PATENT DOCUMENTS 5,348,947 A * 9/1994 Patel ........................... 514/64
5,348,948 A    9/1994 Patel et al.
2004/0224923 A1 11/2004 Lee et al.
2005/0070503 A1  3/2005 Lee et al.

FOREIGN PATENT DOCUMENTS

EP      1155698 A1 * 11/2001
WO  WO 0044387 A1 *  8/2000
WO  WO 00/75142 A2   12/2000
WO  WO 03/059916 A2   7/2003
WO  WO 04/056322 A2   7/2004

OTHER PUBLICATIONS

Snyder et al., J. Med. Liban 48(4): 208-214, 2000.*
Turner et al., Current Pharmaceutical Design. 2, 209-224, 1996.*
Sugar et al., Diagn. Microbiol. Infect. Dis. 21: 129-133, 1995.*
Trujillo et al., Journal of Organometallic Chemistry, 571, 21-29, 1998.*
Bailey, et al., "Boron-Containing Antibacterial Agents: Effects on Growth and Morphology of Bacteria Under Various Culture Conditions," *Antimicrobial Agents and Chemotherapy*, 17(04):549-553, (Apr. 1980).
Brown, et al., "Chiral Synthesis Via Organoboranes. 35. Simple Procedures for the Efficient Recycling of the Terpenyl Chiral Auxiliaries and Convenient Isolation of the Homoallylic Alcohols in Asymmetric Allyl- and Crotylboration of Aldehydes," *J. Org. Chem.*, 57(24):6608-6614, (1992).
Cui, et al., "Organoboron Compounds with an 8-Hydroxyquinolato Chelate and Its Derivatives: Substituent Effects on Structures and Luminescence," *Inorganic Chemistry*, 44(03):601-609, (Feb. 7, 2005), XP002922569.
Farfan, et al., "Through-Bond Modulation on N-B Ring Formation Shown by NMR and X-Ray Diffraction Studies of Borate Derivatives of Pyridyl Alcohols," *J. Chem. Soc. Perkin Trans. 2*. 527-532 (1992).
Guo-Zheng, et al., "Single Site Transarylation of 2,2'-Dimetalized-1,1'-Binaphthyl to Aminocloroborates and Synthesis of 2-Binaphthyl Boron Compounds," *Youji Huaxue/Organic Chemistry, Science Press*, 16(02):139-144, (1996) (XP002922569) (English Abstract).
Koster, et al., "Boron Compounds, XXXIX. Alkenoxy(diorgany)boranes Substituted at the Alkeonxy Group from 2-methylacrolein and triorganylboranes," *Justus Liebigs Annalen Der Chemie*, (06):1116-1134, (1976).
Moeder, et al., "Kinetic Analysis of the Asymmetric Amplification exhibited by B-chlorodiisopinocampheylborane," *Journal of Physical Organic Chemistry*, 17(04):317-324, (Apr. 2004).
Qui, et al., "Luminescent Organoboron Quinolate Polymers," *Journal of the American Chemical Society*, 126(22):7015-7018, (Jun. 9, 2004).

(Continued)

*Primary Examiner*—Venkataraman Balasubramanian
(74) *Attorney, Agent, or Firm*—Morgan, Lewis & Bockius, LLP

(57) ABSTRACT

The structure and preparation of antibiotics incorporating borinic acid complexes are disclosed, especially hydroxyquinoline, imidazole and picolinic acid derivatives, along with compositions of these antibiotics and methods of using the antibiotics and compositions as bactericidal and fungicidal agents as well as therapeutic agents for the treatment of diseases caused by bacteria and fungi.

52 Claims, 2 Drawing Sheets

OTHER PUBLICATIONS

Tabuchi, et al., "Anticoccidial Activity of some Azacyclo Organoborinates," *Heterocycles*, 60(01):177-182, (2003).

Toporcer, et al., "Preparation and Properties of some Tetracoordinate Boron Compounds. The Pseudo-metal Ion Concept," *Inorganic Chemistry*, 4(11):1649-1655, (Nov. 1965).

Zixing, et al., "Synthesis of Aromatic Nitrogen-containing Heterocyclic Derivatives of Asymmetric Diarylborinic Acids," *Wuhan Daxue Xuebo-Wuhan University Journal*, 3:67-71, (1990), XP002922573 (English Abstract).

* cited by examiner

ANTIBIOTICS CONTAINING BORINIC ACID COMPLEXES AND METHODS OF USE

This application is a continuation-in-part of U.S. application Ser. No. 10/740,304, filed 18 Dec. 2003, which claimed priority of U.S. Provisional Applications Ser. No. 60/434,375, filed 18 Dec. 2002, Ser. No. 60/436,095, filed 23 Dec. 2002, and Ser. No. 60/437,849, filed 3 Jan. 2003, the disclosures of all of which are hereby incorporated by reference in their entirety.

FIELD OF THE INVENTION

The present invention relates to the field of antibiotics and particularly antibacterial and antifungal compounds and uses thereof. Methods for preparing and using these antibiotics, and pharmaceutical compositions thereof, are also provided.

BACKGROUND OF THE INVENTION

One hallmark of the modern era of medicine has been the decline in morbidity and mortality associated with bacterial and fungal infections. However, misuse of conventional antibiotics and natural selection of the infectious bacterial population has resulted in the development of varying degrees of drug resistance by most bacterial infectious agents to most antibiotic agents. In severe cases, such as MRSA (Multidrug-Resistant StaphA), one or only a few antibiotics are currently effective. In addition, the existence of immunodeficiency syndromes results in additional incidence of opportunistic infections requiring intensive antibiotic treatment.

Thus, there continues to be a need in the medical arts for novel, more effective, antibiotic compounds, especially for treating bacterial infections, that are resistant to currently available therapies.

Boron containing compounds have received increasing attention as therapeutic agents over the past few years as technology in organic synthesis has expanded to include this atom. [Boron Therapeutics on the horizon, Groziak, M. P.; American Journal of Therapeutics (2001) 8, 321-328] The most notable boron containing therapeutic is the boronic acid bortezomib which was recently launched for the treatment of multiple myeloma. This breakthrough demonstrates the feasibility of using boron containing compounds as pharmaceutical agents. Boron containing compounds have been shown to have various biological activities including herbicides [Organic boron compounds as herbicides. Barnsley, G. E.; Eaton, J. K.; Airs, R. S.; (1957), DE 1016978 19571003], boron neutron capture therapy [Molecular Design and Synthesis of B-10 Carriers for Neutron Capture Therapy. Yamamoto, Y.; Pure Appl. Chem., (1991) 63, 423-426], serine protease inhibition [Borinic acid inhibitors as probes of the factors involved in binding at the active sites of subtilisin Carlsberg and α-chymotrypsin. Simpelkamp, J.; Jones, J. B.; Bioorganic & Medicinal Chemistry Letters, (1992), 2(11), 1391-4], [Design, Synthesis and Biological Evaluation of Selective Boron-containing Thrombin Inhibitors. Weinand, A.; Ehrhardt, C.; Metternich, R.; Tapparelli, C.; Bioorganic and Medicinal Chemistry, (1999), 7, 1295-1307], acetylcholinesterase inhibition [New, specific and reversible bifunctional alkylborinic acid inhibitor of acetylcholinesterase. Koehler, K. A.; Hess, G. P.; Biochemistry (1974), 13, 5345-50] and as antibacterial agents [Boron-Containing Antibacterial Agents: Effects on Growth and Morphology of Bacteria Under Various Culture Conditions. Bailey, P. J.; Cousins, G.; Snow, G. A.; and White, A. J.; Antimicrobial Agents and Chemotherapy, (1980), 17, 549-553]. The boron containing compounds with antibacterial activity can be sub-divided into two main classes, the diazaborinines, which have been known since the 1960's, and dithienylborinic acid complexes. This latter class has been expanded to include many different diarylborinic acid complexes with potent antibacterial activity [Preparation of diarylborinic acid esters as DNA methyl transferase inhibitors. Benkovic, S. J.; Shapiro, L.; Baker, S. J.; Wahnon, D. C.; Wall, M.; Shier, V. K.; Scott, C. P.; Baboval, J.; PCT Int. Appl. (2002), WO 2002044184]. Synthetic developments described in Benkovic et al. enabled creation of a much more diverse class of unsymmetrical di-substituted borinic acid complexes not possible before.

BRIEF SUMMARY OF THE INVENTION

In one aspect, the present invention relates to borinate derivatives as antibiotic compounds especially borinic acid complexes, and include such compounds as derivatives of hydroxyquinolines, picolinic acids and imidazoles.

The antibiotic compounds are also provided as pharmaceutical compositions that can be administered to an animal, most preferably a human, for treatment of a disease having a bacterial or fungal etiology, or an opportunistic infection with a bacteria or fungus in an animal, most preferably a human, in an immunologically compromised or debilitated state of health.

In preferred embodiments, the compounds of the invention are those having the structures given by Formulas 1 or 2, with preferred substituents as disclosed herein.

The invention also provides methods for preparing the antibiotic compounds and pharmaceutical compositions thereof, and methods of using said antibiotics therapeutically. Kits and packaged embodiments of the antibiotic compounds and pharmaceutical compositions of the invention are also contemplated.

The invention also relates to methods of treating infections, preferably bacterial and/or fungal infections, using the antibiotic compounds disclosed herein.

DETAILED DESCRIPTION OF THE INVENTION

Figure 1:
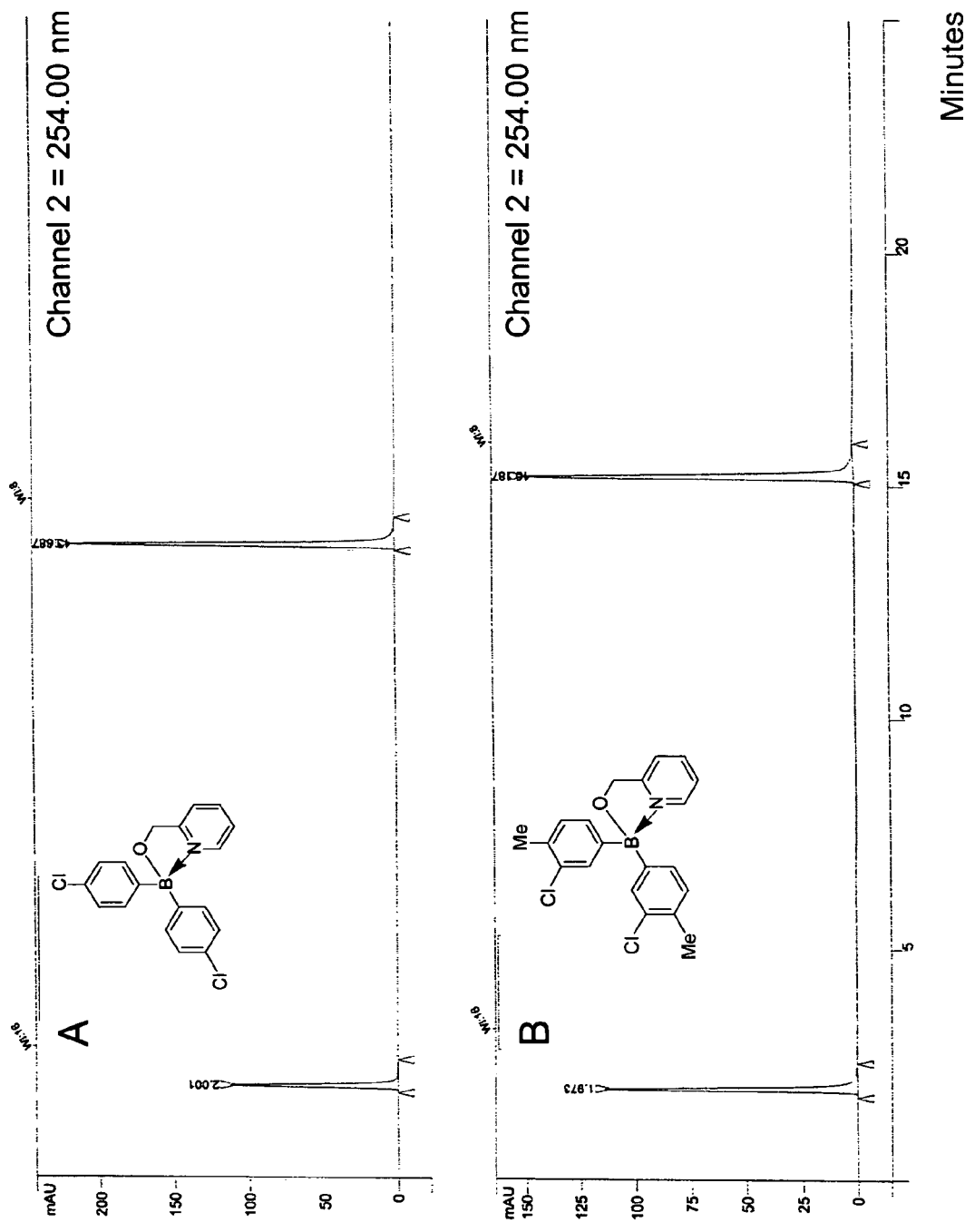
FIG. 1 shows the results of HPLC (high performance liquid chromatography) for several picolinic acid derivatives of the invention.

This invention provides antibiotics, and specifically antibacterial and anti-fungal compounds, useful in treating and/or preventing bacterial infections.

The invention comprises a compound having the structure with formula

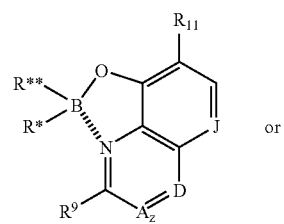

Formula 1 or

-continued

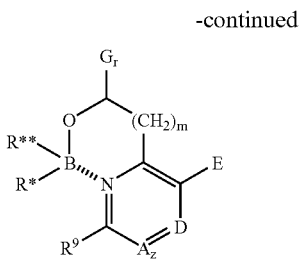

Formula 2 wherein B is boron, O is oxygen wherein R* and R** are each independently selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted phenyl, and substituted or unsubstituted heteroaryl, and wherein z is 0 or 1 and when z is 1, A is CH, $CR^{10}$ or N, and wherein D is N, CH, or $CR^{12}$, and wherein E is H, OH, alkoxy or 2-(morpholino)ethoxy, $CO_2H$ or $CO_2$alkyl and wherein m=0-2, and wherein r is 1 or 2, and wherein when r is 1, G is =O (double-bonded oxygen) and when r is 2, each G is independently H, methyl, ethyl or propyl, wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2N(alkyl)_2$, $SO_2NH$alkyl, $SO_2NH_2$, $SO_2$alkyl, $SO_3H$, $SCF_3$, CN, halogen, $CF_3$, $NO_2$, $NH_2$, 2*-amino, 3*-amino, $NH_2SO_2$ and $CONH_2$, and wherein J is $CR^{10}$ or N and wherein $R^9$, $R^{10}$ and $R^{11}$ are each independently selected from the group consisting of hydrogen, alkyl, cycloalkyl, $(CH_2)_nOH$ (n=2 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$-alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH, including salts thereof.

In preferred embodiments of formula 1 or 2, R* and/or R** are the same or are different, preferably wherein one of R* and R** is a substituted or unsubstituted alkyl ($C_1$-$C_4$) or R* and R** are each a substituted or unsubstituted alkyl ($C_1$-$C_4$).

In a preferred embodiment of formulas 1 or 2, R* and/or R** are the same or are different, preferably wherein one of R* and R** is a substituted or unsubstituted cycloalkyl ($C_3$-$C_7$) or R* and R** are each a substituted or unsubstituted cycloalkyl ($C_3$-$C_7$).

In a preferred embodiment of formulas 1 or 2, R* and/or R** are the same or are different, preferably wherein one of R* and R** is a substituted or unsubstituted alkenyl or R* and R** are each a substituted or unsubstituted alkenyl. In a further preferred embodiment thereof, the alkenyl has the structure

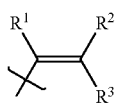

wherein $R^1$, $R^2$, and $R^3$ are each independently selected from the group consisting of hydrogen, alkyl, aryl, cycloalkyl, substituted aryl, aralkyl, substituted aralkyl, $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$ and $NO_2$.

In a preferred embodiment of formulas 1 or 2, R* and/or R** are the same or are different, preferably wherein one of R* and R** is a substituted or unsubstituted alkynyl or R* and R** are each a substituted or unsubstituted alkynyl. In a further preferred embodiment thereof, the alkynyl has the structure

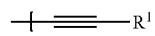

wherein $R^1$ is selected from the group consisting of hydrogen, alkyl, cycloalkyl, aryl, substituted aryl, aralkyl, substituted aralkyl, $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$ and $NO_2$.

In a preferred embodiment of formulas 1 or 2, R* and/or R** are the same or are different, preferably wherein one of R* and R** is a substituted or unsubstituted phenyl or R* and R** are each a substituted or unsubstituted phenyl but excluding compounds of formula 1 wherein z is 1, A is $CR^{10}$, D is $CR^{12}$, J is $CR^{10}$ and excluding compounds of formula 2 wherein the combination of substituents is such that z is 1, A is $CR^{10}$, D is $CR^{12}$, m is 2, and G is H or methyl or ethyl. In a separate embodiment of the foregoing, G is also not propyl. However, in specific embodiments such excluded compounds, although not being claimed as novel, may find use in one or more of the methods of the invention, preferably for treatment against infection, most preferably in treatment against fungal infection. In a preferred embodiment, only novel compounds of the invention are contemplated for such uses.

The novel compounds of the invention do not include quinaldine derivatives, such as 2-methylquinoline, wherein $R^9$ is a methyl, $A_z$ is CH, D is CH, J is CH and $R^{11}$ is hydrogen. However, such compounds may be useful in the methods of the invention.

A preferred embodiment is a compound of Formula 2 wherein R* and R** are each other than a phenyl or substituted phenyl.

Another preferred embodiment is a compound of Formula 2 wherein one of R* or R** is benzyl or substituted benzyl.

An additional preferred embodiment is a compound of Formula 2 wherein r is 1, G is =O, m is 0 and E is OH.

A preferred embodiment is also a compound of Formula 2 wherein z is 1 and $R^9$ is selected from alkyl (greater than $C_4$), $(CH_2)_nOH$ (n=1, 2 or 3), $CH_2NH_2$, $CH_2NH$alkyl, $CH_2N(alkyl)_2$, CHO, CH=NOH, $CO_2H$, $CO_2$-alkyl, S-alkyl, $SO_2$-alkyl, S-aryl, alkoxy (greater than $C_4$), $SCF_3$, and $NO_2$.

In one preferred embodiment the compound has the structure of Formula 2 wherein z is 1 and $R^{10}$ is selected from alkyl (greater than $C_4$), $(CH_2)_nOH$ (n=1, 2 or 3), $CH_2NH_2$, $CH_2NH$alkyl, $CH_2N(alkyl)_2$, CHO, CH=NOH, $CO_2H$, $CO_2$-alkyl, S-alkyl, $SO_2$-alkyl, S-aryl, alkoxy (greater than $C_4$), $SCF_3$, and $NO_2$.

In another preferred embodiment the compound has the structure of Formula 2 wherein z is 1 and D is $CR^{12}$ wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy (greater than $C_4$), aryloxy, SH, S-alkyl, S-aryl, $SO_2$alkyl, $SO_3H$, $SCF_3$, CN, $NO_2$, $NH_2SO_2$ and $CONH_2$.

In an additional preferred embodiment the compound has the structure of Formula 2 wherein z is 1, E is N-(morpholinyl)ethoxy or alkoxy greater than $C_4$.

Other preferred embodiments are compounds having the structure of Formula 2 wherein A or D is nitrogen, or wherein m is 2.

In another preferred embodiment, the compound has the structure of Formula 2 wherein one of R* or R** is substituted phenyl substituted with 1 to 5 substituents each of which is independently selected from alkyl (greater than $C_6$), aryl, substituted aryl, benzyl, substituted benzyl, $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, CONHalkyl, $CON(alkyl)_2$, OH, alkoxy (greater than $C_6$), aryloxy, SH, S-alkyl, S-aryl, $SO_2$alkyl, $SO_3H$, $SCF_3$, CN, $NO_2$, $NH_2$, 2°-amino, 3°-amino, $NH_2SO_2$, $OCH_2CH_2NH_2$, $OCH_2CH_2NHalkyl$, $OCH_2CH_2N(alkyl)_2$, oxazolidin-2-yl, and alkyl substituted oxazolidin-2-yl.

In a further preferred embodiment thereof, the phenyl has the structure

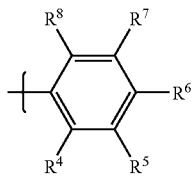

wherein $R^4$, $R^5$, $R^6$, $R^7$ and $R^8$ are each independently selected from the group consisting of hydrogen, alkyl, cycloalkyl aryl, substituted aryl, aralkyl, substituted aralkyl, $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, CONHalkyl, $CON(alkyl)_2$, OH, alkoxy, aryloxy, SH, S-alkyl, S-aryl, $SO_2$alkyl, $SO_2N(alkyl)_2$, $SO_2NHalkyl$, $SO_2NH_2$, $SO_3H$, $SCF_3$, CN, halogen, $CF_3$, $NO_2$, $NH_2$, 2°-amino, 3°-amino, $NH_2SO_2$, $OCH_2CH_2NH_2$, $OCH_2CH_2NHalkyl$, $OCH_2CH_2N(alkyl)_2$, oxazolidin-2-yl, or alkyl substituted oxazolidin-2-yl.

One highly preferred embodiment is a compound of formula 1 wherein R* is 3-fluorophenyl, R** is 4-chlorophenyl, $R^9$ is H, $R^{11}$ is H, $A_z$ is CH, D is CH, J is CH and may be called (3-fluorophenyl)(4-chlorophenyl)borinic acid 8-hydroxyquinoline ester.

Another preferred embodiment is a compound of formula 1 wherein R* and R** are each 3-(4,4-dimethyloxazolidin-2-yl)phenyl, $R^9$ is H, $R^{11}$ is H, $A_z$ is CH, D is CH, J is CH and may be called bis(3-(4,4-dimethyloxazolidin-2-yl)phenyl) borinic acid 8-hydroxyquinoline ester.

An additional preferred embodiment is a compound of formula 1 wherein R* is 3-fluorophenyl, R** is cyclopropyl, $R^9$ is H, $R^{11}$ is H, $A_z$ is CH, D is CH, J is CH and referred to as (3-fluorophenyl)(cyclopropyl)borinic acid 8-hydroxyquinoline ester.

A highly preferred embodiment is a compound of formula 1 wherein R* is 4-(N,N-dimethyl)-aminomethylphenyl, R** is 4-cyanophenyl, $R^9$ is H, $R^{11}$ is H, $A_z$ is CH, D is CH, J is CH and is referred to as (4-(N,N-dimethyl)-aminomethylphenyl)(4-cyanophenyl)borinic acid 8-hydroxyquinoline ester.

Another highly preferred embodiment is a compound of formula 2 wherein R* is the same as R** which is 3-chloro-4-methylphenyl, $R^9$ is H, $R^{11}$ is H, $A_z$ is CH, D is CH and E is OH, m=0, r is 1, G is =O (double bonded oxygen) and is referred to as bis(3-chloro-4-methylphenyl)borinic acid 3-hydroxypicolinate ester.

A further highly preferred embodiment is a compound of formula 2 wherein R* is the same as R** which is 2-methyl-4-chlorophenyl, $R^9$ is H, $R^{11}$ is H, $A_z$ is CH, D is CH and E is OH, m=0, r is 1, G is =O (double bonded oxygen) and is referred to as bis(2-methyl-4-chlorophenyl)borinic acid 3-hydroxypicolinate ester.

In a preferred embodiment of formula 1 or 2, R* and/or R** are the same or are different, preferably wherein one of R* and R** is a substituted or unsubstituted benzyl or R* and R** are each a substituted or unsubstituted benzyl. In a further preferred embodiment thereof, the benzyl has the structure

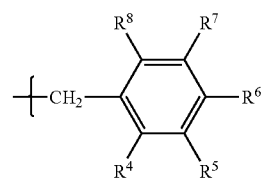

wherein $R^4$, $R^5$, $R^6$, $R^7$ and $R^8$ are each independently selected from the group consisting of alkyl, cycloalkyl, aryl, substituted aryl, aralkyl, substituted aralkyl, $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, CONHalkyl, $CON(alkyl)_2$, OH, alkoxy, aryloxy, SH, S-alkyl, S-aryl, $SO_2$alkyl, $SO_2N(alkyl)_2$, $SO_2NHalkyl$, $SO_2NH_2$, $SO_3H$, $SCF_3$, CN, halogen, $CF_3$, $NO_2$, $NH_2$, 2°-amino, 3°-amino, $NH_2SO_2$, $OCH_2CH_2NH_2$, $OCH_2CH_2NHalkyl$, $OCH_2CH_2N(alkyl)_2$, oxazolidin-2-yl, or alkyl substituted oxazolidin-2-yl.

One preferred embodiment is a compound of formula 1 or 2, R* and/or R** are the same or are different, preferably wherein one of R* and R** is a substituted or unsubstituted heterocycle or R* and R** are each a substituted or unsubstituted heterocycle. In a further preferred embodiment thereof, the heterocycle has the structure

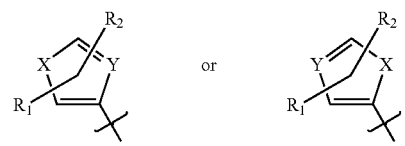

wherein X=CH=CH, N=CH, $NR^{13}$ (wherein $R^{13}$=H, alkyl, aryl or aralkyl), O, or S and wherein Y=CH or N and wherein $R^1$, $R^2$, and $R^3$ are each independently selected from the group consisting of hydrogen, alkyl, cycloalkyl, aryl, substituted aryl, aralkyl, substituted aralkyl, $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, S-alkyl, S-aryl, $SO_2$alkyl, $SO_2N(alkyl)_2$, $SO_2NHalkyl$, $SO_2NH_2$, $SO_3H$, $SCF_3$, CN, halogen, $CF_3$, $NO_2$, oxazolidin-2-yl, or alkyl substituted oxazolidin-2-yl.

A highly preferred embodiment is a compound of formula 1 wherein R* is pyrid-3-yl, R** is 4-chlorophenyl, $R^9$ is H, $R^{11}$ is H, $A_z$ is CH, D is CH, and J is CH (named (pyrid-3-yl)(4-chlorophenyl)borinic acid 8-hydroxyquinoline ester).

A highly preferred embodiment is a compound of formula 1 wherein R* is 5-cyanopyrid-3-yl, R** is vinyl, $R^9$ is H, $R^{11}$ is H, $A_z$ is CH, D is CH, and J is CH (named (5-cyanopyrid-3-yl)(vinyl)borinic acid 8-hydroxyquinoline ester).

One preferred embodiment is a compound of formula 1 wherein $R^9$ is H, $R^{11}$ is H, $A_z$ is CH, D is CH, and J is CH.

Another preferred embodiment is a compound of formula 2 wherein $R^9$ is H, $R^{11}$ is H, $A_z$ is CH, D is CH and E is OH, m=0, r is 1, and G is =O (double bonded oxygen).

The structures of the invention also permit solvent interactions that may afford structures (such as Formulas 1B and 2B) that include atoms derived from the solvent encountered by the compounds of the invention during synthetic procedures and therapeutic uses. Thus, such solvent structures can especially insinuate themselves into at least some of the compounds of the invention, especially between the boron and nitrogen atoms, to increase the ring size of such compounds by one or two atoms. For example, where the boron ring of a structure of the invention comprises 5 atoms, including, for example, the boron, a nitrogen, an oxygen and 2 carbons, insinuation of a solvent atom between the boron and nitrogen would afford a 7 membered ring. In one example, use of hydroxyl and amino solvents may afford structures containing an oxygen or nitrogen between the ring boron and nitrogen atoms to increase the size of the ring. Such structures are expressly contemplated by the present invention, preferably where R*** is H or alkyl

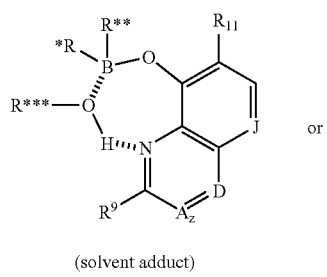

Formula 1B (solvent adduct)

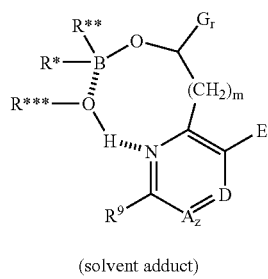

Formula 2B (solvent adduct)

As used herein, the following terms have the stated meaning:

By "alkyl", "lower alkyl", and "$C_1$-$C_6$ alkyl" in the present invention is meant straight or branched chain alkyl groups having 1-6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "alkoxy", "lower alkoxy", and "$C_1$-$C_6$ alkoxy" in the present invention is meant straight or branched chain alkoxy groups having 1-6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By the term "halogen" in the present invention is meant fluorine, bromine, chlorine, and iodine.

By "cycloalkyl", e.g., $C_3$-$C_7$ cycloalkyl, in the present invention is meant cycloalkyl groups having 3-7 atoms such as, for example cyclopropyl, cyclobutyl, cyclopentyl, cyclohexyl, and cycloheptyl. In $C_3$-$C_7$ cycloalkyl groups, preferably in $C_5$-$C_7$ cycloalkyl groups, one or two of the carbon atoms forming the ring can be replaced with a hetero atom, such as sulfur, oxygen or nitrogen. Examples of such groups are piperidinyl, piperazinyl, morpholinyl, pyrrolidinyl, imidazolidinyl, oxazolidinyl, perhydroazepinyl, perhydrooxazapinyl, oxepanyl, and perhydrooxepanyl. $C_3$ and $C_4$ cycloalkyl groups having a member replaced by nitrogen or oxygen include aziridinyl, azetidinyl, oxetanyl, and oxiranyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy. Preferred aryl groups include phenyl and naphthyl, each of which is optionally substituted as defined herein.

By "heteroaryl" is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, napthyridinyl, benzimidazolyl, and benzoxazolyl. Preferred heteroaryls are thiazolyl, pyrimidinyl, preferably pyrimidin-2-yl, and pyridyl. Other preferred heteroaryl groups include 1-imidazolyl, 2-thienyl, 1-(or 2-)quinolinyl, 1-(or 2-)isoquinolinyl, 1-(or 2-)tetrahydroisoquinolinyl, 2-(or 3-)furanyl and 2-tetrahydro-furanyl.

By "ligand" is meant a nitrogen-containing aromatic system which is capable of forming a dative bond with the Lewis acidic boron center, while appended as a borinate ester moiety. Such ligands are known to those trained in the arts. Examples are shown in the structures below.

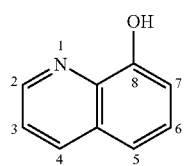 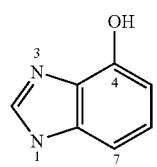

8-hydroxyquinoline     4-hydroxybenzimidazole

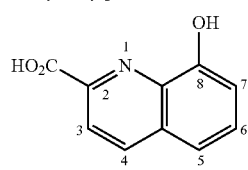 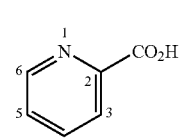

8-hydroxyquinoline-2-carboxylic acid     picolinic acid (pyridine-2-carboxylic acid)

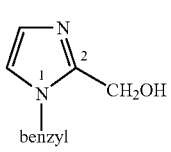 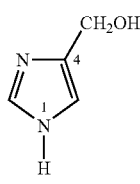

2-hydroxymethyl-1N-benzylimidazole     4-hydroxymethyl-imidazole

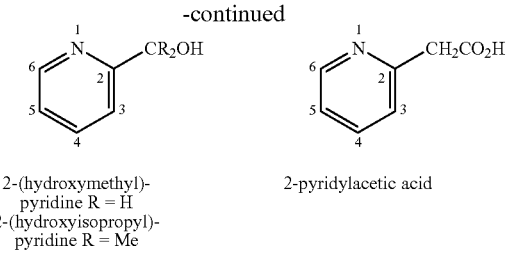

2-(hydroxymethyl)-pyridine R = H
2-(hydroxyisopropyl)-pyridine R = Me 2-pyridylacetic acid The compounds of the present invention have been implicated in the inhibition of key microbial enzymes, such as bacterial DNA methyltransferase. Many of the compounds disclosed herein are selective inhibitors of methyltransferases in microbes, while not inhibitory for methyltransferases in mammals. However, the anti-bacterial and anti-fungal activity of the compounds of the invention is not limited to those with said enzyme inhibitory activity, nor is the latter effect necessarily essential to said therapeutic activity.

The invention also provides embodiments of the compounds disclosed herein as pharmaceutical compositions. The pharmaceutical compositions of the present invention can be manufactured in a manner that is itself known, e.g., by means of a conventional mixing, dissolving, granulating, dragee-making, levigating, emulsifying, encapsulating, entrapping or lyophilizing processes.

Pharmaceutical compositions for use in accordance with the present invention thus can be formulated in conventional manner using one or more physiologically acceptable carriers comprising excipients and auxiliaries that facilitate processing of the active compounds into preparations that can be used pharmaceutically. Proper formulation is dependent upon the route of administration chosen.

Non-toxic pharmaceutical salts include salts of acids such as hydrochloric, phosphoric, hydrobromic, sulfuric, sulfinic, formic, toluenesulfonic, methanesulfonic, hydroxyethanesulfonic, nitric, benzoic, citric, tartaric, maleic, fumaric hydroiodic, alkanoic such as acetic, $HOOC-(CH_2)_n-CH_3$ where n is 0-4, and the like. Non-toxic pharmaceutical base addition salts include salts of bases such as sodium, potassium, calcium, ammonium, and functional equivalents. Those skilled in the art will recognize a wide variety of non-toxic pharmaceutically acceptable addition salts.

For injection, the compounds of the invention can be formulated in appropriate aqueous solutions, such as physiologically compatible buffers such as Hanks's solution, Ringer's solution, or physiological saline buffer. For transmucosal and transcutaneous administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, capsules, liquids, gels, syrups, slurries, suspensions and the like, for oral ingestion by a patient to be treated. Pharmaceutical preparations for oral use can be obtained with solid excipient, optionally grinding a resulting mixture, and processing the mixture of granules, after adding suitable auxiliaries, if desired, to obtain tablets. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler, can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system can be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can substitute for dextrose.

Alternatively, other delivery systems for hydrophobic pharmaceutical compounds can be employed. Liposomes and emulsions are well known examples of delivery vehicles or carriers for hydrophobic drugs. Certain organic solvents such as dimethyl sulfoxide also can be employed, although usually at the cost of greater toxicity. Additionally, the compounds can be delivered using a sustained-release system, such as semipermeable matrices of solid hydrophobic polymers containing the therapeutic agent. Various sustained-release materials have been established and are well known by those skilled in the art. Sustained-release capsules can, depending on their chemical nature, release the compounds for a few weeks up to over 100 days. Depending on the chemical nature and the biological stability of the therapeutic reagent, additional strategies for protein and nucleic acid stabilization can be employed.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The compounds of the invention can be provided as salts with pharmaceutically compatible counterions. Pharmaceutically compatible salts can be formed with many acids, including but not limited to hydrochloric, sulfuric, acetic, lactic, tartaric, malic, succinic, phosphoric, hydrobromic, sulfinic, formic, toluenesulfonic, methanesulfonic, nitic, benzoic, citric, tartaric, maleic, hydroiodic, alkanoic such as acetic, $HOOC-(CH_2)_n-CH_3$ where n is 0-4, and the like. Salts tend to be more soluble in aqueous or other protonic solvents that are the corresponding free base forms. Non-toxic pharmaceutical base addition salts include salts of bases such as sodium, potassium, calcium, ammonium, and the like. Those skilled in the art will recognize a wide variety of non-toxic pharmaceutically acceptable addition salts.

For topical administration, the compounds can be formulated readily by combining the active compounds with pharmaceutically acceptable carriers well known in the art. Such carriers enable the compounds of the invention to be formulated as gels, slurries, suspensions and ointments for topical applications. If desired, disintegrating agents can be added, such as the cross-linked polyvinyl pyrrolidone, agar, or alginic acid or a salt thereof such as sodium alginate.

Pharmaceutical compositions of the compounds of the present invention can be formulated and administered through a variety of means, including systemic, localized, or topical administration. Techniques for formulation and administration can be found in "Remington's Pharmaceutical Sciences," Mack Publishing Co., Easton, Pa. The mode of administration can be selected to maximize delivery to a desired target site in the body. Suitable routes of administration can, for example, include oral, rectal, transmucosal, transcutaneous, or intestinal administration. Parenteral delivery, including intramuscular, subcutaneous, and intramedullary injections, as well as intrathecal, direct intraventricular, intravenous, intraperitoneal, intranasal, or intraocular injections are also contemplated.

Alternatively, one can administer the compound in a local rather than systemic manner, for example, via injection of the compound directly into a specific tissue, often in a depot or sustained release formulation.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of bacterial cell growth. Such information can be used to more accurately determine useful doses in humans.

It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician.

For administration to non-human animals, the drug or a pharmaceutical composition containing the drug may also be added to the animal feed or drinking water. It will be convenient to formulate animal feed and drinking water products with a predetermined dose of the drug so that the animal takes in an appropriate quantity of the drug along with its diet. It will also be convenient to add a premix containing the drug to the feed or drinking water approximately immediately prior to consumption by the animal.

Preferred compounds of the invention will have certain pharmacological properties. Such properties include, but are not limited to, oral bioavailability, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcová et al. (1996, *J. Chromat B* 677: 1-27). Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population).

The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g. Fingl et al, 1975, in "The Pharmacological Basis of Therapeutics", Ch.1, p.1).

Dosage amount and interval can be adjusted individually to provide plasma levels of the active moiety that are sufficient to maintain bacterial cell growth inhibitory effects. Usual patient dosages for systemic administration range from 100-2000 mg/day. Stated in terms of patient body surface areas, usual dosages range from 50-910 mg/m²/day. Usual average plasma levels should be maintained within 0.1-1000 µM. In cases of local administration or selective uptake, the effective local concentration of the compound cannot be related to plasma concentration.

The compounds of the invention are useful as antibiotics for the treatment of diseases of both animals and humans, including but not limited to actinomycosis, anthrax, bacterial dysentery, botulism, brucellosis, cellulitis, cholera, conjunctivitis, cystitis, diphtheria, bacterial endocarditis, epiglottitis, gastroenteritis, glanders, gonorrhea, Legionnaire's disease, leptospirosis, bacterial meningitis, plague, bacterial pneumonia, puerperal sepsis, rheumatic fever, Rocky Mountain spotted fever, scarlet fever, streptococcal pharyngitis, syphilis, tetanus, tuberculosis, tularemia, typhoid fever, typhus, and pertussis.

The disclosures in this application of all articles and references, including patents and patent applications, are incorporated herein by reference in their entirety.

The compounds of the invention comprise a novel class of broad-spectrum antibiotics. Medically-important bacterial species that provide appropriate targets for the antibacterial activity of the inhibitors of the invention include gram-positive bacteria, including cocci such as *Staphylococcus* species and *Streptococcus* species; acid-fast bacterium, including *Mycobacterium* species; bacilli, including *Bacillus* species, *Corynebacterium* species and *Clostridium* species; filamentous bacteria, including *Actinomyces* species and *Streptomyces* species; gram-negative bacteria, including cocci such as *Neisseria* species and *Acinetobacter* species; bacilli, such as *Pseudomonas* species, *Brucella* species, *Agrobacterium* species, *Bordetella* species, *Escherichia* species, *Shigella* species, *Yersinia* species, *Salmonella* species, *Klebsiella* species, *Enterobacter* species, *Haemophilus* species, *Pasteurella* species, and *Streptobacillus* species; spirochetal species, *Campylobacter* species, *Vibrio* species; and intracellular bacteria including *Rickettsiae* species and *Chlamydia* species.

Specific bacterial species that are targets for the antibiotics of the invention include *Staphylococcus aureus; Staphylococcus epidermidis, Staphylococcus saprophyticus; Streptococcus pyogenes; Streptococcus agalactiae; Streptococcus pneumoniae; Enterococcus faecalis; Enterococcus faecium; Bacillus anthracis; Mycobacterium avium, Mycobacterium tuberculosis, Acinetobacter baumannii; Corynebacterium diphtheria; Clostridium perfringens; Clostridium botulinum; Clostridium tetani; Neisseria gonorrhoeae; Neisseria meningitidis; Pseudomonas aeruginosa; Legionella pneumophila; Escherichia coli; Yersinia pestis; Haemophilus influenzae; Helicobacter pylori; Campylobacter fetus; Campylobacter jejuni; Vibrio cholerae; Vibrio parahemolyticus; Trepomena pallidum; Actinomyces israelii; Rickettsia prowazekii; Rickettsia rickettsii; Chlamydia trachomatis; Chlamydia psittaci; Brucella abortus; Agrobacterium tumefaciens*; and *Francisella tularensis*.

Medically-important fungal and yeast species that provide appropriate targets for the antifungal activity of the inhibitors of the invention include *Candida albicans, Candida glabrata, Candida krusei, Candida parapsilosis, Trichophyton mentagrophytes, Microporium canis, Aspergillus* species, *Cryptococcus neoformans, Blastomyces dermatitidis, Coccidiodes immitis, Histoplasma capsulatum* and *Paracoccidioides brasiliensis*.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those skilled in the art will have sufficient knowledge of such systems and methodologies so as to be able, without undue experimentation, to make such substitutions as will optimally serve their purposes in using the methods and procedures disclosed herein.

The invention is described in more detail in the following non-limiting examples. It is to be understood that these methods and examples in no way limit the invention to the embodiments described herein and that other embodiments and uses will no doubt suggest themselves to those skilled in the art.

The compounds of this invention are evaluated for their antibacterial activity as per the guidelines and procedures prescribed by the National Committee for Clinical Laboratory Standards (NCCLS) (cf., NCCLS Document M7-A3, 1993 —Antimicrobial Susceptibility Testing).

Protocol for MIC Determination

A useful protocol for MIC determination is as follows:
1. Approximately 2.5 mg of the compounds to be tested was weighed into cryovials.
2. 5 mg/ml stock solutions were made by adding DMSO to the samples accordingly.
3. 256 µg/ml working solutions were made by using the 5 mg/ml stock solutions and adding sterile distilled water accordingly.
4. A Beckman 2000 Automated Workstation was programmed to load 96 well plates with broth and compounds as follows:

100 µl of the appropriate broth was added to columns 1-11
   200 µl of the appropriate broth was added to column 12
   100 µl of compounds at the 256 µg/ml working solution were added to column 1 (one compound per row)
   Two-fold serial dilutions were done from column 1 to 10
   Column 11 served as the growth control
5. The 10 organism panel was plated from stock vials stored at −80° C. and incubated for 24 hours at 34° C. The organisms were then sub-cultured and incubated for 24 hours at 34° C.

The inoculums were first prepared in sterile distilled water with a target of 0.09-0.11 absorbance at 620 nm wavelength
   A 1/100 dilution was made into the appropriate broth
   100 µl of broth with organism was added to columns 1-11
   Column 12 served as the blank control 6. The completed 96 well plates were incubated for 24 hours at 34° C. The 96 well plates were then read using a Beckman Automated Plate Reader at 650 nm wavelength. The MIC was determined through calculations involving the growth control (column 11) and blank control (column 12).

Protocol for Antifungal In Vitro MIC Determination

A useful protocol for antifungal activity determination is described below.

Preparation

Media is prepared 1-2 weeks before the start of the experiment. Media is stored in the cold room (4° C.) prior to use.

Sabouraud Dextrose Agar Plates:
1. Add 65 g of powdered of Sabouraud Dextrose Agar media into 1 L of $dH_2O$ with gentle stirring
2. Autoclave at 121° C. and 22 psi for 15 minutes
3. Allow the media to cool to ~50° C.
4. Pour media into 100×15 mm sterile petri dishes with 20 ml aliquots RPMI 1640+MOPS Broth:
1. Add 1 packet of powdered RPMI media to 1 L of $dH_2O$ (15° C.-30° C.) with gentle stirring
2. Add 2 g of $NaHCO_3$
3. Add 34.5 g of MOPS
4. Adjust the pH to 7.0 using NaOH or HCl
5. Sterilize with membrane filtration (0.22 micron cellulose acetate filter)

Sterile Saline (0.9%)
1. Dissolve 9 g of NaCl to 1 L of $dH_2O$
2. Autoclave at 121° C. and 22 psi for 15 minutes Sterile $dH_2O$
1. Autoclave $dH_2O$ at 121° C. and 22 psi for 15 minutes Procedure
1. The 10 organism panel is plated from stock vials stored at −80° C. (suspended in broth with 20% glycerol) and incubated at 37° C. for 24 hours. The organisms are then sub-cultured and incubated at 37° C. for 24 hours. These will be used to prepare fresh inoculums for Step 6.
2. Approximately 2.5 mg of the compounds to be tested are weighed into 2 ml cryovials. Fluconazole, Amphotericin B and Itraconazole are tested as reference compounds.
3. 5 mg/ml stock solutions are made by adding DMSO to the samples accordingly. Compounds insoluble with vortexing only are sonicated.
4. 256 μg/ml working solutions are made by using the 5 mg/ml stock solutions and adding sterile distilled water accordingly.
5. 96-well plates are used for MIC determination. Each of the 8 rows can be used to test a different compound. Compounds are loaded into the first column and two-fold dilutions of are made from column 1 to 10. Column 11 is a growth control (no compound) and column 12 is a blank control (no compound or organism). Manual addition of broth and compounds is performed as follows:

100 μl of RPMI+MOPS broth is added to columns 1-11
200 μl of RPMI+MOPS broth is added to column 12
100 μl of compounds at the 256 μg/ml working solution are added to column 1 (one compound per row)
Two-fold serial dilutions are done from column 1 to 10
Column 11 serves as the growth control (media+organism only)

6. The sub-cultured organisms are used to prepare fresh inoculums for testing on the 96-well plates. Each 96-well plate will test a different organism.
Colonies from the sub-cultured organisms (Step 1) are used to prepare inoculums with sterile saline. The target is adjusted to 70-75% transmittance at 530 nm wavelength using a Novospec II spectrophotometer.

1/1000 dilution is made into RPMI+MOPS broth
100 μl of this broth with organism is added to columns 1-11 (column 12 serves as the blank control)

7. The completed 96-well plates are incubated at 37° C. for 24 hours. The 96 well plates are then read for absorbance at 650 nm wavelength using a Biomek Automated Plate Reader.

Calculations

The absorbance readings from the Biomek Automated Plate Reader are used to determine the percent inhibition for each test well. The formula used is as follows:

% Inhibition=$[1-(ABS_{test}-ABS_{blank})/(ABS_{mean\ growth}-ABS_{blank})]\times 100\%$ $ABS_{test}$: Absorbance of the test well
$ABS_{blank}$: Absorbance of the blank well in the same row as the test well (column 12)
$ABS_{mean\ growth}$: Mean absorbance of the growth control wells (column 11)

The minimum inhibitory concentration (MIC) is found at the lowest concentration of compound where percent inhibition is greater than or equal to 80%.

These procedures were used to obtain the results in the following tables. Representative microbiological data for the compounds 10 to 123 are shown in Tables 1 to 4 as MIC (Minimum Inhibitory Concentration) with the values expressed as micrograms per ml.

Thus, the invention provides antibiotics that are generically called borinic acid complexes, most preferably derived from disubstituted borinic acids.

Borinate Complexes

The synthesis of the compounds of the invention is accomplished in several formats. Reaction scheme #1 demonstrates the synthesis of the intermediate borinic acids, and their subsequent conversion to the desired borinic acid complexes. When R* and R** are identical, the reaction of two equivalents of an arylmagnesium halide (or aryllithium) with trialkyl borate, followed by acidic hydrolysis affords the desired borinic acid 5. When R* and R** are not identical, the reaction of one equivalent of an arylmagnesium halide (or aryllithium) with appropriate aryl(dialkoxy)borane (4), heteroaryl(dialkoxy)borane or alkyl(dialkoxy)borane (alkoxy group comprised of methoxy, ethoxy, isopropoxy, or propoxy moiety), followed by acidic hydrolysis affords the unsymmetrical borinic acids 6 in excellent yields. Where applicable, the reaction of the alkylene esters (3, T=nothing, $CH_2$, $CMe_2$) with the appropriate organocerium, organolithium, organomagnesium or equivalent reactant is convenient.

As shown in Scheme 1, the borinic acid complexes are obtained from the precursor borinic acids by reaction with one equivalent of the desired heterocyclic ligand in suitable solvents (i.e., ethanol, isopropanol, dioxane, ether, toluene, dimethylformamide, N-methylpyrrolidone, or tetrahydrofuran).

Scheme 1

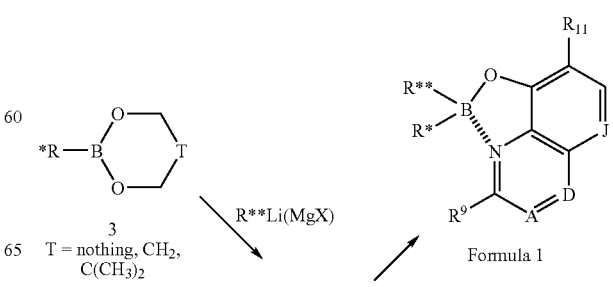

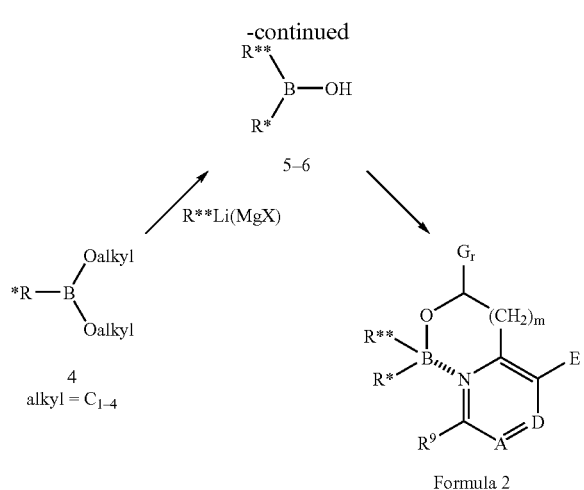

Formula 2

In certain situations, compounds of the invention may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Unexpected Stability of Picolinic Acid Complexes

Figure 2:
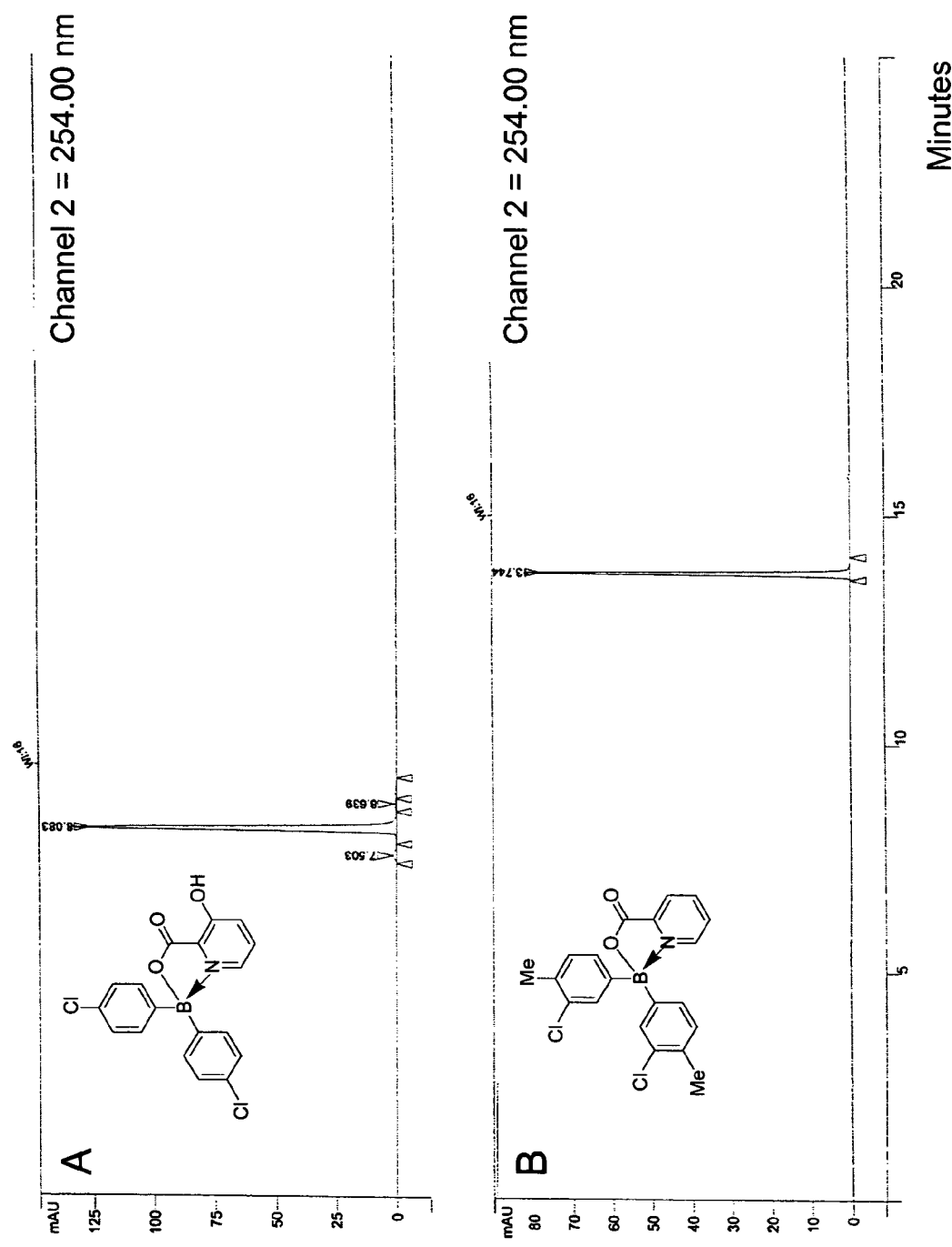
FIG. 2 shows the results of HPLC (high performance liquid chromatography) for several picolinic acid derivatives of the invention.

During the preparation of compounds of Formula 2 we found that complexes containing hydroxymethyl-type borinic esters, e.g., 2-hydroxymethyl-pyridine ($R^9$ is H, A is CH, D is CH, E is H, m is 0, r is 2, G is H) were not stable under typical HPLC conditions. For example, the 2-hydroxymethylpyridine complexes shown in FIGS. 1A and 1B both eluted as two peaks, one with the solvent front and one much later, indicating some manner of degradation had occurred during the HPLC process. This posed a serious problem. Instability issues prevent this class of compound from being developed as drug candidates. However, it was subsequently found that picolinic acid complexes (e.g., $R^9$ is H, A is CH, D is CH, E is H, m is 0, r is 1, G is =O (double bonded oxygen)) were stable under identical the same HPLC conditions. For example, the picolinic acid complexes shown in FIGS. 2A and 2B show the complex to elute as a single peak indicating no breakdown of the complex. The biological activities of the picolinic acid class are comparable to or better than the hydroxymethyl pyridine complexes making the picolinic acid complexes an ideal drug development candidate.

HPLC Conditions

| Sample preparation: | ~1 mg/mL dissolved in 100% acetonitrile |
| --- | --- |
| Column: | BetaBasic C18 5 um 150 × 4.6 mm |
| Flow rate: | 1 mL/min |
| Injection vol: | 10 uL |
| Wavelength: | PDA 200–450 nm; 254 nm reported |
| Mobile phase: | Solvent A: 0.1% $H_3PO_4$ in water |
|  | Solvent B: Acetonitrile |

| Gradient Method: | | |
| --- | --- | --- |
| Time (min) | % A | % B |
| 0 | 95 | 5 |
| 1 | 95 | 5 |
| 11 | 0 | 100 |
| 21 | 0 | 100 |

Representative compounds of the present invention include, but are not limited to, the compounds disclosed herein and their pharmaceutically acceptable acid and base addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. In a preferred embodiment, the compounds of the invention comprise any of compounds 10-123 (Tables 1, 2, 3 and 4), and variants thereof.

TABLE 1

Antibacterial Profile Against Select Gram-positive and Gram-negative Pathogens

| Cmp | R* | R** | Ligand | S. aureus ATCC 29213 | S. epidermidis ATCC 12228 | S. pneumoniae ATCC 6301 | E. faecalis ATCC 29212 | E. faecium CT-26 | M. catarrhalis ATCC 25238 |
| --- | --- | --- | --- | --- | --- | --- | --- | --- | --- |
| 10 | 3-$ClC_6H_4$ | 3-$ClC_6H_4$ | 8-hydroxyquinoline | 1 | 2 | 2 | 32 | 4 | NA |
| 11 | 4-Me-3-$ClC_6H_3$ | 4-Me-3-$ClC_6H_3$ | 4-hydroxybenzimidazole | 0.125 | 4 | NA | 8 | 8 | NA |
| 12 | 3-$ClC_6H_4$ | 3-$ClC_6H_4$ | 5-fluoro-8-hydroxyquinoline | 0.125 | 2 | 2 | 8 | 4 | 2 |
| 13 | 3-$ClC_6H_4$ | 3-$ClC_6H_4$ | 5-chloro-8-hydroxyquinoline | 0.125 | 1 | 1 | 64 | 2 | 0.25 |
| 14 | 3-$ClC_6H_4$ | 3-$ClC_6H_4$ | 4-methyl-8-hydroxyquinoline | 0.125 | 1 | 1 | 64 | 4 | 0.5 |
| 15 | 2-F-4-$ClC_6H_3$ | 3-$FC_6H_4$ | 8-hydroxyquinoline | 0.125 | 1 | 2 | 16 | 4 | 0.5 |
| 16 | 4-Me-3-$ClC_6H_3$ | 4-Me-3-$ClC_6H_3$ | 2-$HO_2$C-4-hydroxy-5,7-dichloroquinoline | 0.25 | 0.5 | NA | 0.5 | 0.25 | NA |
| 17 | 3-$ClC_6H_4$ | 3-$ClC_6H_4$ | 2-amino-8-hydroxyquinoline | 0.25 | 2 | 2 | 8 | 8 | 2 |
| 18 | 3-$ClC_6H_4$ | 3-Cl-4-$FC_6H_3$ | 8-hydroxyquinoline | 0.25 | 1 | 2 | 8 | 4 | 1 |
| 19 | 3-$ClC_6H_4$ | 3-$ClC_6H_4$ | 5-cyano-8-hydroxyquinoline | 0.25 | 2 | 4 | 16 | 4 | 0.5 |

TABLE 1-continued

Antibacterial Profile Against Select Gram-positive and Gram-negative Pathogens

| Cmp | R* | R** | Ligand | S. aureus ATCC 29213 | S. epidermidis ATCC 12228 | S. pneumoniae ATCC 6301 | E. faecalis ATCC 29212 | E. faecium CT-26 | M. catarrhalis ATCC 25238 |
|---|---|---|---|---|---|---|---|---|---|
| 20 | 3-ClC$_6$H$_4$ | 3-Cl-5-FC$_6$H$_3$ | 8-hydroxyquinoline | 0.25 | 1 | 2 | 8 | 4 | 2 |
| 21 | 3-ClC$_6$H$_4$ | 3-FC$_6$H$_4$ | 5-cyano-8-hydroxyquinoline | 0.5 | 4 | 2 | 16 | 8 | 0.25 |
| 22 | 3-ClC$_6$H$_4$ | 3-FC$_6$H$_4$ | 5-nitro-8-hydroxyquinoline | 0.5 | 4 | 2 | 64 | 16 | 0.12 |
| 23 | 3-ClC$_6$H$_4$ | 3-FC$_6$H$_4$ | 5-chloro-7-chloro-8-hydroxyquinoline | 0.5 | 16 | 8 | 64 | 16 | 0.12 |
| 24 | 3-ClC$_6$H$_4$ | 3-FC$_6$H$_4$ | 5-bromo-7-bromo-8-hydroxyquinoline | 0.5 | 8 | 8 | 64 | 32 | 0.12 |
| 25 | 3-ClC$_6$H$_4$ | 3-ClC$_6$H$_4$ | 2-carboxy-4-hydroxy-8-methoxyquinoline | 0.5 | 8 | 2 | 16 | 16 | 2 |
| 26 | 2-thienyl | Me | 8-hydroxyquinoline | 0.5 | 1 | NA | 4 | 4 | NA |
| 27 | 3-NCC$_6$H$_4$ | 4-Me-3-ClC$_6$H$_3$ | 8-hydroxyquinoline | 0.5 | 1 | 1 | 8 | 2 | 1 |
| 28 | 3,4-Cl$_2$C$_6$H$_3$ | 3-FC$_6$H$_4$ | 8-hydroxyquinoline | 0.5 | 1 | 2 | 4 | 2 | 1 |
| 29 | 2,4-Cl$_2$C$_6$H$_3$ | 3-FC$_6$H$_4$ | 8-hydroxyquinoline | 0.5 | 1 | 2 | 8 | 2 | 0.5 |
| 30 | 3,4-Cl$_2$C$_6$H$_3$ | 3,4-Cl$_2$C$_6$H$_3$ | 8-hydroxyquinoline | 1 | 0.5 | NA | 2 | 2 | NA |
| 31 | 4-Me-3-ClC$_6$H$_3$ | 4-Me-3-ClC$_6$H$_3$ | 2-carboxy-4-hydroxyquinoline | 1 | 1 | NA | 2 | 1 | NA |
| 32 | 3-ClC$_6$H$_4$ | 3-FC$_6$H$_4$ | 8-hydroxyquinoline | 1 | 1 | 1 | 16 | 2 | 2 |
| 33 | 3-Cl-5-FC$_6$H$_3$ | 3-MeC$_6$H$_4$ | 8-hydroxyquinoline | 1 | 1 | 1 | 8 | 2 | 2 |
| 34 | 3-ClC$_6$H$_4$ | 3-FC$_6$H$_4$ | 5-fluoro-8-hydroxyquinoline | 1 | 2 | 2 | 8 | 4 | 1 |
| 35 | 3-ClC$_6$H$_4$ | 3-MeSC$_6$H$_4$ | 5-fluoro-8-hydroxyquinoline | 1 | 2 | 2 | 8 | 4 | 2 |
| 36 | 3-ClC$_6$H$_4$ | 2-thienyl | 8-hydroxyquinoline | 1 | 1 | 2 | 8 | 2 | 4 |
| 37 | 3-Me-4-ClC$_6$H$_3$ | 3-NCC$_6$H$_4$ | 8-hydroxyquinoline | 1 | 1 | 1 | 8 | 2 | 1 |
| 38 | 2-FC$_6$H$_4$ | 3-NCC$_6$H$_4$ | 8-hydroxyquinoline | 1 | 1 | 2 | 16 | 2 | 1 |
| 39 | 3-ClC$_6$H$_4$ | 3-NCC$_6$H$_4$ | 8-hydroxyquinoline | 1 | 1 | 1 | 8 | 2 | 2 |
| 40 | 3-NCC$_6$H$_4$ | Vinyl | 8-hydroxyquinoline | 1 | 1 | 1 | 8 | 2 | 2 |
| 41 | 3-NCC$_6$H$_4$ | Ethynyl | 8-hydroxyquinoline | 1 | 1 | 1 | 4 | 2 | 1 |
| 42 | 3-FC$_6$H$_4$ | Ethynyl | 8-hydroxyquinoline | 1 | 1 | 1 | 8 | 2 | 1 |
| 43 | 2-ClC$_6$H$_4$ | Ethynyl | 8-hydroxyquinoline | 1 | 1 | 1 | 8 | 2 | 1 |
| 44 | Ethynyl | Ethynyl | 8-hydroxyquinoline | 1 | 1 | 1 | 16 | 2 | 0.25 |
| 45 | 3,5-F$_2$C$_6$H$_3$ | Ethynyl | 8-hydroxyquinoline | 1 | 1 | 1 | 8 | 1 | 1 |
| 46 | 3,5-Cl$_2$C$_6$H$_3$ | Ethynyl | 8-hydroxyquinoline | 1 | 1 | 1 | 4 | 1 | 1 |
| 47 | 3,4-Cl$_2$C$_6$H$_3$ | Ethynyl | 8-hydroxyquinoline | 1 | 1 | 1 | 8 | 2 | 1 |
| 48 | 3-Cl-4-FC$_6$H$_3$ | Ethynyl | 8-hydroxyquinoline | 1 | 1 | 1 | 8 | 2 | 2 |
| 49 | 4-ClC$_6$H$_4$ | 4-ClC$_6$H$_4$ | 5-chloro-8-hydroxyquinoline | 2 | 1 | 1 | 16 | 2 | 0.25 |
| 50 | 4-ClC$_6$H$_4$ | 4-ClC$_6$H$_4$ | 8-hydroxyquinoline | 2 | 2 | 2 | 4 | 4 | NA |
| 51 | 3-FC$_6$H$_4$ | 3-FC$_6$H$_4$ | 8-hydroxyquinoline | 2 | 1 | NA | 8 | 2 | NA |
| 52 | 4-Me-3-ClC$_6$H$_3$ | 4-Me-3-ClC$_6$H$_3$ | 8-hydroxyquinoline | 2 | 4 | NA | 8 | 16 | NA |
| 53 | 3-NCC$_6$H$_4$ | 3-NCC$_6$H$_4$ | 8-hydroxyquinoline | 2 | 2 | NA | 64 | 4 | 2 |
| 54 | 4-ClC$_6$H$_4$ | 4-Cl-3-FC$_6$H$_3$ | 8-hydroxyquinoline | 2 | 1 | 2 | 8 | 4 | 1 |
| 55 | 4-Cl-3-FC$_6$H$_3$ | 4-Cl-3-FC$_6$H$_3$ | 8-hydroxyquinoline | 2 | 1 | 2 | 4 | 2 | 4 |
| 56 | 3-MeC$_6$H$_4$ | 3,5-Cl$_2$C$_6$H$_3$ | 8-hydroxyquinoline | 2 | 2 | 2 | 8 | 4 | 4 |
| 57 | 4-ClC$_6$H$_4$ | 4-FC$_6$H$_4$ | 5-fluoro-8-hydroxyquinoline | 2 | 2 | 4 | 16 | 4 | 1 |
| 58 | 3-ClC$_6$H$_4$ | 4-FC$_6$H$_4$ | 5-fluoro-8-hydroxyquinoline | 2 | 2 | 2 | 8 | 4 | 0.5 |
| 59 | 3-ClC$_6$H$_4$ | 4-MeSC$_6$H$_4$ | 8-hydroxyquinoline | 2 | 1 | 1 | 8 | 4 | 2 |
| 60 | 4-ClC$_6$H$_4$ | 3-MeSC$_6$H$_4$ | 8-hydroxyquinoline | 2 | 1 | 2 | 8 | 4 | 2 |
| 61 | 3-ClC$_6$H$_4$ | cyclopropyl | 8-hydroxyquinoline | 2 | 1 | 1 | 16 | 2 | 2 |
| 62 | 4-ClC$_6$H$_4$ | 3-MeSC$_6$H$_4$ | 5-fluoro-8-hydroxyquinoline | 2 | 2 | 2 | 8 | 4 | 2 |
| 63 | 4-ClC$_6$H$_4$ | 4-MeSC$_6$H$_4$ | 8-hydroxyquinoline | 2 | 1 | 2 | 8 | 4 | 1 |
| 64 | 4-ClC$_6$H$_4$ | 4-MeSC$_6$H$_4$ | 5-fluoro-8-hydroxyquinoline | 2 | 2 | 4 | 8 | 8 | 1 |
| 65 | 4-ClC$_6$H$_4$ | 4-Cl-3-HOC$_6$H$_3$ | 8-hydroxyquinoline | 2 | 2 | 2 | 16 | 4 | 4 |
| 66 | 4-ClC$_6$H$_4$ | 3-FC$_6$H$_4$ | 4-methyl-8-hydroxyquinoline | 2 | 1 | 1 | 64 | 4 | 0.5 |
| 67 | 3-ClC$_6$H$_4$ | 3-(DMISO)C$_6$H$_4$ | 4-methyl-8-hydroxyquinoline | 2 | 1 | 1 | 64 | 4 | 0.5 |
| 68 | 3-FC$_6$H$_4$ | 3-(DMISO)C$_6$H$_4$ | 8-hydroxyquinoline | 2 | 2 | 16 | 32 | 4 | 0.12 |
| 69 | 3-(DMISO)C$_6$H$_4$ | cyclopropyl | 8-hydroxyquinoline | 2 | 1 | 2 | 64 | 4 | 1 |
| 70 | 3-FC$_6$H$_4$ | cyclopropyl | 8-hydroxyquinoline | 2 | 1 | 1 | 64 | 2 | 0.5 |
| 71 | 3-FC$_6$H$_4$ | 4-NCC$_6$H$_4$ | 5-chloro-7-chloro-8-hydroxyquinoline | 2 | 2 | 8 | 64 | 4 | 0.12 |
| 72 | 3-(DMISO)C$_6$H$_4$ | 3-(DMISO)C$_6$H$_4$ | 8-hydroxyquinoline | 4 | 2 | 4 | 64 | 4 | NA |
| 73 | 3-(DMISO)C$_6$H$_4$ | Vinyl | 8-hydroxyquinoline | 2 | 1 | 2 | 64 | 8 | 0.25 |
| 74 | 4-FC$_6$H$_4$ | 4-NCC$_6$H$_4$ | 8-hydroxyquinoline | 2 | 1 | 2 | 32 | 2 | 1 |
| 75 | 3-ClC$_6$H$_4$ | 3-MeSC$_6$H$_4$ | 8-hydroxyquinoline | 2 | 1 | 2 | 64 | 4 | NA |

TABLE 1-continued

Antibacterial Profile Against Select Gram-positive and Gram-negative Pathogens

| Cmp | R* | R** | Ligand | S. aureus ATCC 29213 | S. epidermidis ATCC 12228 | S. pneumoniae ATCC 6301 | E. faecalis ATCC 29212 | E. faecium CT-26 | M. catarrhalis ATCC 25238 |
|---|---|---|---|---|---|---|---|---|---|
| 76 | 4-Me-3-ClC$_6$H$_3$ | 2-thienyl | 8-hydroxyquinoline | 2 | 1 | NA | 8 | 4 | NA |
| 77 | 3-ClC$_6$H$_4$ | 2-MeC$_6$H$_4$ | 8-hydroxyquinoline | 2 | 1 | 1 | 8 | 4 | 2 |
| 78 | 3-ClC$_6$H$_4$ | 2-MeOC$_6$H$_4$ | 8-hydroxyquinoline | 2 | 1 | 1 | 8 | 2 | 2 |
| 79 | 3-ClC$_6$H$_4$ | 2-Me-4-ClC$_6$H$_3$ | 8-hydroxyquinoline | 2 | 2 | 2 | 8 | 4 | 2 |
| 80 | 4-Cl-3-MeC$_6$H$_3$ | 4-Cl-3-MeC$_6$H$_3$ | 8-hydroxyquinoline | 2 | 1 | 2 | 4 | 4 | 2 |
| 81 | 3-ClC$_6$H$_4$ | 3-Cl-6-MeOC$_6$H$_3$ | 8-hydroxyquinoline | 2 | 1 | 2 | 8 | 4 | 2 |
| 82 | 3,5-Cl$_2$C$_6$H$_3$ | 4-(Me$_2$NC$_2$H$_4$)OC$_6$H$_4$ | 8-hydroxyquinoline | 2 | 2 | 2 | 8 | 2 | 4 |
| 83 | 4-BrC$_6$H$_4$ | 4-(Me$_2$NC$_2$H$_4$)OC$_6$H$_4$ | 8-hydroxyquinoline | 2 | 1 | 2 | 4 | 4 | 2 |
| 84 | 3-ClC$_6$H$_4$ | 4-F-3-MeC$_6$H$_3$ | 8-hydroxyquinoline | 2 | 1 | 2 | 8 | 4 | 4 |
| 85 | 3-Me-4-ClC$_6$H$_3$ | 3-F-4-ClC$_6$H$_3$ | 8-hydroxyquinoline | 2 | 1 | 2 | 4 | 4 | 2 |
| 86 | 3-FC$_6$H$_4$ | 4-Cl-3-MeC$_6$H$_3$ | 8-hydroxyquinoline | 2 | 1 | 2 | 8 | 4 | 2 |
| 87 | 3-FC$_6$H$_4$ | 3-F-4-ClC$_6$H$_3$ | 8-hydroxyquinoline | 2 | 1 | 2 | 8 | 4 | 1 |
| 88 | 3-Cl-6-FC$_6$H$_3$ | 3-NCC$_6$H$_4$ | 8-hydroxyquinoline | 2 | 2 | 2 | 8 | 2 | 2 |
| 89 | 2,5-F$_2$C$_6$H$_3$ | 3-NCC$_6$H$_4$ | 8-hydroxyquinoline | 2 | 1 | 1 | 8 | 2 | 2 |
| 90 | 4-F-3-ClC$_6$H$_3$ | 3-NCC$_6$H$_4$ | 8-hydroxyquinoline | 2 | 2 | 1 | 8 | 2 | 2 |
| 91 | 3-Me-4-ClC$_6$H$_3$ | 4-NCC$_6$H$_4$ | 8-hydroxyquinoline | 2 | 1 | 2 | 8 | 2 | 1 |
| 92 | 2,5-F$_2$C$_6$H$_3$ | 4-NCC$_6$H$_4$ | 8-hydroxyquinoline | 2 | 1 | 2 | 8 | 4 | 1 |
| 93 | 3-Cl-6-FC$_6$H$_3$ | 4-NCC$_6$H$_4$ | 8-hydroxyquinoline | 2 | 1 | 1 | 8 | 4 | 1 |
| 94 | 3-Cl-6-MeOC$_6$H$_3$ | 4-NCC$_6$H$_4$ | 8-hydroxyquinoline | 2 | 1 | 1 | 8 | 4 | 2 |
| 95 | 4-NCC$_6$H$_4$ | Ethynyl | 8-hydroxyquinoline | 2 | 1 | 2 | 8 | 2 | 1 |
| 96 | 4-ClC$_6$H$_4$ | 3,4-F$_2$C$_6$H$_3$ | 8-hydroxyquinoline | 2 | 1 | 2 | 8 | 2 | 1 |
| 97 | 4-ClC$_6$H$_4$ | 4-Me-3-FC$_6$H$_3$ | 8-hydroxyquinoline | 2 | 1 | 1 | 8 | 2 | 1 |
| 98 | 4-ClC$_6$H$_4$ | 3,5-F$_2$C$_6$H$_3$ | 8-hydroxyquinoline | 2 | 1 | 1 | 8 | 4 | 1 |
| 99 | 3-CF$_3$-4-ClC$_6$H$_3$ | 3-FC$_6$H$_4$ | 8-hydroxyquinoline | 2 | 1 | 2 | 8 | 2 | 1 |
| 100 | 4-ClC$_6$H$_4$ | 3-F-5-CF$_3$C$_6$H$_3$ | 8-hydroxyquinoline | 2 | 1 | 2 | 4 | 2 | 1 |
| Ciprofloxacin | | | | 0.125 | 0.125 | 0.5 | 0.5 | 64 | 0.125 |
| Cloxacillin | | | | 0.125 | 0.25 | 0.125 | 16 | 64 | 1 |
| Imipenem | | | | 0.125 | 0.125 | 0.125 | 1 | 64 | 0.125 |
| Ceftriaxone | | | | 2 | 1 | 0.125 | 64 | 64 | 0.125 |
| Meropenem | | | | 0.06 | 0.06 | | 2 | | |
| Erythromycin | | | | 0.5 | 0.5 | | 2 | | |
| Pen G | | | | 0.5 | 16 | 0.125 | 1 | 32 | 0.125 |

DMISO = 4,4-dimethyloxazolin-2-yl

TABLE 2

Antibacterial Profile Against Select Gram-positive and Gram-negative Pathogens

| Cmp | R* | R** | Ligand | S. aureus ATCC 29213 | S. epidermidis ATCC 12228 | S. pneumonia ATCC 6301 | E. faecalis ATCC 29212 | E. faecium CT-26 | H. influenzae ATCC 49766 |
|---|---|---|---|---|---|---|---|---|---|
| 101 | 3-ClC$_6$H$_4$ | 3-ClC$_6$H$_4$ | 1-(2-morpholino-4-yl-ethyl)-imidazoleacetate | 0.12 | 4 | 16 | 64 | 64 | 4 |
| 102 | 3-ClC$_6$H$_4$ | 3-ClC$_6$H$_4$ | 2-hydroxyisopropyl-3-hydroxypyridine | 0.5 | 1 | 0.25 | 64 | 2 | 64 |
| 103 | 4-ClC$_6$H$_4$ | 4-ClC$_6$H$_4$ | 2-hydroxyisopropyl-3-hydroxypyridine | 0.25 | 0.5 | 0.5 | 4 | 1 | 64 |
| 104 | 4-Me-3-ClC$_6$H$_3$ | 4-Me-3-ClC$_6$H$_3$ | 2-hydroxymethyl-1N-benzylimidazole | 0.5 | 4 | NA | 16 | 32 | 8 |
| 105 | 3-ClC$_6$H$_4$ | 3-ClC$_6$H$_4$ | 2-hydroxymethylpyridine | 0.125 | 4 | 4 | 32 | 32 | 4 |
| 106 | 4-Me-3-ClC$_6$H$_3$ | 4-Me-3-ClC$_6$H$_3$ | 2-pyridylacetic acid | 0.5 | 4 | NA | 64 | 64 | 64 |
| 107 | 4-Me-3-ClC$_6$H$_3$ | 4-Me-3-ClC$_6$H$_3$ | 3-(2-hydroxyethoxy)-picolinic acid | 0.125 | 4 | NA | 16 | 8 | 32 |
| 108 | 4-Me-3-ClC$_6$H$_3$ | 4-Me-3-ClC$_6$H$_3$ | 3-(N-morpholinylethoxy)-picolinic acid | 0.25 | 4 | NA | 4 | 2 | 64 |
| 109 | 4-Me-3-ClC$_6$H$_3$ | 4-Me-3-ClC$_6$H$_3$ | 3-(OCH$_2$CH$_2$CH$_2$CO$_2$H)-picolinic acid | 1 | 4 | 4 | 32 | 16 | 16 |
| 110 | 4-Me-3-ClC$_6$H$_3$ | 4-Me-3-ClC$_6$H$_3$ | 3-carboxypicolinic acid | 0.125 | 4 | NA | 8 | 8 | 8 |
| 111 | 4-Me-3-ClC$_6$H$_3$ | 4-Me-3-ClC$_6$H$_3$ | 3-hydroxypicolinic acid | 2 | 1 | NA | 2 | 2 | 64 |
| 112 | 4-Me-3-ClC$_6$H$_3$ | 4-CH$_3$C$_6$H$_4$ | 3-hydroxypicolinic acid | 4 | 2 | NA | 4 | 8 | 64 |
| 113 | 4-Me-3-ClC$_6$H$_3$ | Phenylethyl | 3-hydroxypicolinic acid | 0.5 | 1 | NA | 2 | 64 | 64 |
| 114 | 3-ClC$_6$H$_4$ | 3-ClC$_6$H$_4$ | 3-hydroxypicolinic acid | 0.125 | 8 | NA | 64 | 64 | 16 |
| 115 | 4-EtO-3-ClC$_6$H$_3$ | 4-EtO-3-ClC$_6$H$_3$ | 3-hydroxypicolinic acid | 2 | 2 | 1 | 8 | 16 | 64 |
| 116 | 2-Cl-5-Br-6-FC$_6$H$_2$ | 2-F-4-ClC$_6$H$_3$ | 3-hydroxypicolinic acid | 2 | 1 | 0.25 | 4 | 4 | 64 |

TABLE 2-continued

Antibacterial Profile Against Select Gram-positive and Gram-negative Pathogens

| Cmp | R* | R** | Ligand | S. aureus ATCC 29213 | S. epidermidis ATCC 12228 | S. pneumonia ATCC 6301 | E. faecalis ATCC 29212 | E. faecium CT-26 | H. influenzae ATCC 49766 |
|---|---|---|---|---|---|---|---|---|---|
| 117 | 2-Me-4-ClC$_6$H$_3$ | 3-ClC$_6$H$_4$ | 3-hydroxypicolinic acid | 2 | 1 | 0.5 | 4 | 4 | 16 |
| 118 | 2-Me-4-ClC$_6$H$_3$ | 2-Me-4-ClC$_6$H$_3$ | 3-hydroxypicolinic acid | 1 | 0.25 | 0.12 | 1 | 1 | 16 |
| 119 | 4-Me-3-ClC$_6$H$_3$ | 4-Me-3-ClC$_6$H$_3$ | 3-OAc-picolinic acid | 2 | 1 | NA | 2 | 2 | 64 |
| 120 | 4-Me-3-ClC$_6$H$_3$ | 4-Me-3-ClC$_6$H$_3$ | 4-hydroxybenzimidazole | 0.125 | 4 | NA | 8 | 8 | |
| 121 | 3-ClC$_6$H$_4$ | 3-ClC$_6$H$_4$ | 4-hydroxyethylimidazole | 0.125 | 4 | 8 | 32 | 32 | 4 |
| 122 | 3-ClC$_6$H$_4$ | 3-ClC$_6$H$_4$ | 6-amino-3-hydroxypicolinic acid | 0.25 | 4 | 16 | 32 | 32 | 8 |
| 123 | 3-ClC$_6$H$_4$ | 3-ClC$_6$H$_4$ | Imidazole acetic acid | 0.125 | 2 | 8 | 32 | 32 | 8 |
| Ceftriaxone | | | | 2 | 1 | <0.125 | 64 | 64 | 0.12 |
| Ciprofloxacin | | | | 0.12 | 0.12 | 0.5 | 0.5 | 64 | 0.12 |
| Cloxacillin | | | | 0.12 | 0.25 | 0.12 | 16 | 64 | 8 |
| Erythromycin | | | | 0.5 | 0.5 | NA | 2 | NA | 4 |
| Imipenem | | | | 0.12 | 0.12 | <0.125 | 1 | 64 | 2 |
| Meropenem | | | | 0.06 | 0.06 | NA | 2 | NA | 0.06 |
| Pen G | | | | 0.5 | 16 | <0.125 | 1 | 32 | 0.12 |

TABLE 3

Anti-mycobacterium In vitro Activity

| | M. tuberculosis MIC (mcg/mL) | | |
|---|---|---|---|
| Compound | H37Rv* | P2SP1** | P1SP2** |
| 10 | 0.387 | 0.387 | 0.387 |
| 50 | 0.387 | 0.387 | 0.387 |
| 51 | 0.387 | 0.387 | 0.387 |
| 53 | 0.775 | 0.775 | 0.387 |
| 55 | 0.775 | 0.775 | 0.387 |
| 65 | 0.775 | 0.775 | 0.775 |
| 72 | 0.775 | 0.775 | 0.775 |
| 75 | 0.775 | 0.775 | 0.775 |
| Isoniazid (INH) | <0.062 | >8 | >8 |
| Rifampicin | <0.125 | 16 | >16 |
| Ethambutol | <1 | 8 | 8 |
| Ethionamide | 1 | >64 | 32 |
| p-aminosalicylate | <0.25 | 32 | 16 |
| Ofloxacin | 4 | 32 | 16 |
| Streptomycin | <2 | <2 | <2 |
| Kanamycin | <2 | <2 | <2 |
| cycloserine | 8 | 8 | 8 |

*Sensitive strain
**Multi-drug resistant strain

TABLE 4

Antifungal Activity for Select Borinic Acid Complexes

| | MIC (μg/ml) | | | | | |
|---|---|---|---|---|---|---|
| Compound | Candida albicans ATCC 90028 | Candida glabrata ATCC 15126 | Candida parapsilosis ATCC 22019 | Microsporum canis ATCC 10214 | Aspergillus fumigatus ATCC 204305 | Trichophyton mentagrophytes ATCC 10270 |
| 53 | 1 | >32 | 32 | 16 | >32 | >32 |
| 124 | 1 | >32 | 32 | 16 | >32 | >32 |
| 125 | 1 | >32 | 32 | 16 | >32 | >32 |
| 126 | 1 | >32 | 32 | 16 | >32 | >32 |
| 127 | 1 | >32 | 16 | 16 | >32 | 32 |
| 128 | 1 | 32 | 16 | 12 | >32 | 16 |
| 129 | 1 | >32 | 32 | 16 | >32 | 32 |
| 130 | 1 | 0.5 | 0.5 | 0.5 | 0.5 | 0.5 |
| 131 | 2 | >32 | >32 | 32 | >32 | 32 |
| 132 | 2 | 1 | 0.5 | 0.38 | >32 | 0.25 |
| Amphotericin B | 1 | 0.75 | 0.75 | 0.5 | 1 | 1 |
| Fluconazole | 0.25 | 3 | 2.5 | 16 | >64 | 16 |

The present invention also encompasses the acylated prodrugs of the compounds of the invention. Those skilled in the art will recognize various synthetic methodologies which may be employed to prepare non-toxic pharmaceutically acceptable addition salts and acylated prodrugs of the inventive compounds.

Tables 1 to 4 also contain inhibitory activity for known antibiotics, shown at the end of each of the tables.

EXAMPLES

Proton NMR are recorded on Varian AS 400 and MercuryPlus 300 MHz spectrometer and chemical shifts are reported as δ (ppm) down field from tetramethylsilane. Mass spectra are determined on Micromass Quattro II and Applied Biosystems AP3000. Compound numbers appear in parentheses and correspond to numbers in Tables 1 to 4.

Formation of Ethylene Glycol Boronate Ester (3, T=nothing)

General Procedure

Boronic acid was dissolved in dry THF, dry toluene or dry diethyl ether (~10 mL/g) under nitrogen. Ethylene glycol (1 molar equivalent) was added to the reaction and the reaction was heated to reflux for 1 to 4 hours. Reaction was cooled to room temperature and solvent was removed under reduced pressure leaving the ethylene glycol ester as an oil or a solid. In cases where an oil was obtained or a solid that dissolved in hexane, dry hexane was added and removed under reduced pressure. The product was then placed under high vacuum for several hours. In cases where a solid was obtained that did not dissolve in hexane, the solid was collected by filtration and washed with cold hexane.

3-Cyanophenylboronic acid ethylene glycol ester (3a)

3-Cyanophenyl boronic acid (1 g, 6.8 mmol) was dissolved in dry THF (10 mL) under nitrogen. Ethylene glycol (379 μL, 422 mg, 6.8 mmol) was added and the reaction was heated to reflux for 4 hours then cooled to room temperature. THF was removed by rotary evaporator to give a white solid. Cold hexane was added and the product was collected by filtration giving a white solid (1.18 g, quant. yield). $^1$H-NMR (300.058 MHz, DMSO-d6) δ ppm 7.92-8.01 (3H, m), 7.50-7.64 (1H, m), 4.35 (4H, s)

Thiophene 3-boronic acid ethylene glycol ester (3b)

Thiophene-3-boronic acid (1 g, 7.8 mmol) was dissolved in dry THF (10 mL) under nitrogen. Ethylene glycol (435 μL, 484 mg, 7.8 mmol) was added and the reaction was heated to reflux for 1 hour then cooled to room temperature. THF was removed by rotary evaporator to give a white solid. Hexane was added, dissolving the solid and removed by rotary evaporation. The product was placed under high vacuum to yield a tan solid (1.17 g, 97%). $^1$H-NMR (300.058 MHz, CDCl$_3$) δ ppm 7.93 (1H, s), 7.3-7.4 (2H, m), 4.35 (4H, s).

3-Fluorophenylboronic acid ethylene glycol ester (3c)

A mixture of 3-fluorophenylboronic acid (7.00 g, 50.0 mmol) and ethylene glycol (2.8 mL, 50 mmol) in toluene (200 mL) was heated to reflux for 3 hours under Dean-Stark conditions. The solvent was removed under reduced pressure to afford 3-fluorophenylboronic acid ethylene glycol ester (7.57 g, 91%).

Formation of Unsymmetrical Borinic Acid (6) from Boronic Acid Ethylene Glycol Ester General Procedure A: Grignard Methodology Boronic acid ethylene glycol ester was dissolved in dry THF (10-20 mL/g) under nitrogen. Solution was cooled to −78° C. in an acetone/dry ice bath or to 0° C. in an ice/water bath. Grignard reagent (0.95 to 1.2 molar equivalent) was added dropwise to the cooled solution. The reaction was warmed to room temperature and stirred for 3-18 hours. 6N HCl (2 mL/g) was added and solvent was removed under reduced vacuum. Product was extracted into diethyl ether (40 mL/g) and washed with water (3×equal volume). Organic layer was dried (MgSO$_4$), filtered and the solvent was removed by rotary evaporation giving the crude product, which is either purified by column chromatography or taken onto the next step without purification. Alternative work-up: if the borinic acid product contained a basic group such as an amine or pyridine, then after stirring at room temperature for 3-18 hours, water (2 mL/g) was added and the pH adjusted to 5-8. Product was extracted into diethyl ether or ethyl acetate or THF up to three times (40 mL/g). Organic layer was dried (MgSO$_4$), filtered and the solvent was removed by rotary evaporation giving the crude product, which is either purified by column chromatography or taken onto the next step without purification.

(4-Cyanophenyl)(3-fluorophenyl)borinic acid (6a)

4-Cyanophenyl boronic acid ethylene glycol ester (500 mg, 2.89 mmol) was dissolved in dry THF under nitrogen. The solution was cooled to −78° C. in an acetone/dry ice bath and 3-fluorophenylmagnesium bromide (1M in THF)(2.74 mL, 2.74 mmol, 0.95 molar equivalent) was added dropwise to the cold solution. The reaction was allowed to warm slowly to room temperature and stirred for 18 hours. 6N HCl (1 mL) was added to the reaction causing a cloudy appearance and the solvent was removed using a rotary evaporator. The product was extracted into diethyl ether (20 mL) and washed with water (3×20 mL). The organic layer was dried (MgSO4), filtered and the solvent removed using a rotary evaporator to yield the crude product as an oily solid. This was taken onto the next step without purification.

General Procedure B: (Hetero)aryl-lithium Methodology

The (hetero)aryl-bromide or iodide was dissolved in dry THF (20-30 mL/g) under nitrogen and degassed. The solution was cooled to −78° C. in an acetone/dry ice bath and n-, sec- or tert-butyllithium in THF or other solvent (1.2-2.4 molar equivalents) was added to the cooled solution dropwise (generally causing the solution to turn deep yellow). The boronic acid ethylene glycol ester (1 molar equivalent) was dissolved in dry THF or diethyl ether (2-10 mL/g) under nitrogen. The boronic acid ethylene glycol ester in THF was added dropwise to the cooled aryl-lithium solution (generally causing the solution to turn pale yellow). The reaction was warmed to room temperature and stirred for 1-18 hours. 6N HCl (2-4 mL/g) was added and solvent was removed under reduced vacuum. Product was extracted into diethyl ether (40 mL/g) and washed with water (3×equal volume). Organic layer was dried (MgSO$_4$), filtered and the solvent was removed by rotary evaporation giving the crude product, which is either purified by column chromatography or taken onto the next step without purification. Alternative work-up: if the borinic acid product contained a basic group such as an amine or pyridine then after stirring at room temperature for 3-18 hours water (2 mL/g) was added and the pH adjusted to 5-8. Product was extracted into diethyl ether or ethyl acetate or THF up to

(3-Thienyl)(3-chlorophenyl)borinic acid (6b)

3-Chloro-bromobenzene (447 µL, 728 mg, 3.8 mmol) was dissolved in dry THF (15 mL) under nitrogen. The solution was degassed and cooled to −78° C. in an acetone/dry ice bath. tert-Butyllithium (1.7M in THF)(4.47 mL, 7.6 mmol, 2 molar equivalent) was added to the cooled solution dropwise causing the solution to turn deep yellow. The solution was stirred at −78° C. while 3-thiopheneboronic acid ethylene glycol ester (586 mg) was dissolved in dry diethyl ether (1 mL). The boronic ester solution was then added dropwise to the cooled solution causing the color to change to pale yellow. The reaction was warmed to room temperature and stirred for 18 hours. 6N HCl (2 mL) was added and the reaction was stirred for 1 hour. The solvent was removed using a rotary evaporator. The product was extracted into diethyl ether (10 mL) and washed with water (2×10 mL). The organic layer was dried (MgSO4), filtered and the solvent removed using a rotary evaporator to yield the crude product as an orange oil. The product was purified by column chromatography using silica gel and hexane: ethyl acetate 5:1 as eluent giving the pure product as a clear oil (614 mg, 73%).

(3-Chlorophenyl)vinylborinic acid (6c)

This was prepared by a similar process as described for 6b by the reaction of 3-cyanophenyl boronic acid ethylene glycol ester with vinyllithium.

(3-Fluoro-5-chlorophenyl)ethynylborinic acid (6d)

This was prepared by a similar process as described for 6b by the reaction of 3-fluoro-5-chlorophenyl boronic acid ethylene glycol ester with ethynyllithium.

(4-Methyl-3-chlorophenyl)(2-thienyl)borinic acid (6e)

This was prepared by a similar process as described for 6b by the reaction of 2-thienylboronic acid ethylene glycol ester with 4-methyl-3-chlorophenyllithium.

(4-Cyanophenyl)ethynylborinic acid (6f)

This was prepared by a similar process as described for 6b by the reaction of 4-cyanophenylboronic acid ethylene glycol ester with ethynyllithium.

(3-Fluorophenyl)cyclopropylborinic acid (6q)

This was prepared by a similar process as described for 6b by the reaction of 3-fluorophenylboronic acid ethylene glycol ester with cyclopropyllithium.

(3-Thienyl)methylborinic acid (6h)

This was prepared by a similar process as described for 6b by the reaction of 3-thienylboronic acid ethylene glycol ester with methyllithium.

(4-Pyridyl)phenylborinic acid (6i)

This was prepared by a similar process as described for 6b by the reaction of phenylboronic acid ethylene glycol ester with 4-pyridyllithium.

(3-Cyanophenyl)(2-fluorophenyl)borinic acid (6j)

This was prepared by a similar process as described for 6b by the reaction of 3-cyanophenylboronic acid ethylene glycol ester with 2-fluorophenyllithium.

4-(Dimethylaminomethyl)phenyl 3-fluorophenyl borinic acid (6k)

Sec-butyllithium (1.4 M in cyclohexane, 6.0 mL) was added to a solution of N,N-dimethyl-4-bromobenzylamine (1.50 g, 7.00 mmol) in THF (14 mL) at −78° C. under nitrogen atmosphere and the mixture was stirred for 15 min. 3-Fluorophenylboronic acid ethylene glycol ester (1.16 g, 7.00 mmol) in THF (7 mL) was added to the mixture. The reaction was allowed to warm to room temperature and stirred for 1 h. Water was added and the mixture was washed with ether. The pH was adjusted to 8 with 1M hydrochloric acid. The mixture was extracted with ethyl acetate twice. The organic layer was washed with brine and dried on anhydrous sodium sulfate. The solvent was removed under reduced pressure to afford the borinic acid (890 mg, 49%).

Formation of Symmetrical Borinic Acid (5) by Reaction of Organometallics with Trialkyl Borates.

Bis(4-chlorophenyl)borinic acid (5a) (Procedure C)

A cold solution (−78° C.) of trimethyl borate (0.37 ml) in dry tetrahydrofuran (THF, 25 ml) was treated dropwise with 4-chlorophenylmagnesium bromide (6.75 ml, 1M solution in ether). The reaction mixture was stirred at −78° C. for 1 h and then stirred for 18 h at room temperature. The solvent was removed under reduced pressure. The resultant residue was stirred with 100 ml of ether and 15 ml of 6N hydrochloric acid. Organic layer was separated and aqueous layer was extracted with ether (2×100 ml). The combined organic extract was washed with brine and dried over anhydrous magnesium sulfate. Solvent was removed to give light yellowish solid. The product was chromatographed over silica gel (Hex:Ether=1:1) to give 420 mg of borinic acid. $^1$H NMR (400 MHz, CDCl$_3$) δ: 5.84 (s, OH), 7.46 (d, 4H, Ar—H), 7.72 (d, 4H, Ar—H).

Bis(3-Chloro-4-methylphenyl)borinic acid (5b)

In a similar manner as for 5a, the titled compound was obtained from the reaction of 3-chloro-4-methylphenylmagnesium bromide with trimethyl borate. The product was obtained by chromatography over silica gel.

Bis(3-Fluoro-4-methylphenyl)borinic acid (5c)

In a similar manner as for 5a, the titled compound was obtained from the reaction of 3-fluoro-4-methylphenyllithium with trimethyl borate. The product was obtained by chromatography over silica gel.

Bis(3-Chloro-4-methoxyphenyl)borinic acid (5d)

In a similar manner as for 5a, the titled compound was obtained from the reaction of 3-chloro-4-methoxyphenyl-

Bis(3-Fluoro-4-methoxyphenyl)borinic acid (5e)

In a similar manner as for 5a, the titled compound was obtained from the reaction of 3-fluoro-4-methoxyphenyl-lithium with trimethyl borate. The product was obtained by chromatography over silica gel.

Formation of Unsymmetrical Borinic Acids (6) by Reaction of Organometallics with alkyl(or aryl or alkenyl)dialkoxyboranes.

(4-Chloro-phenyl)methyl-borinic acid (6m) (Procedure D)

To 4-chlorophenylmagnesium bromide (5.5 ml, 1M solution in ether) at −78° C., di(isopropoxy)methylborane (1 ml, 0.78 g) was added dropwise via syringe. The reaction mixture was stirred at −78° C. for 1 h and then stirred overnight at ambient temperature. The reaction mixture was treated dropwise with 100 ml of ether and 15 ml of 6N hydrochloric acid, and stirred for 1 h. Organic layer was separated and aqueous layer was extracted with ether (2×100 ml). The combined organic extract was washed with brine and dried over anhydrous sodium sulfate. Solvent was removed under reduce pressure to give 1.1 g of oil. $^1$H NMR of the product was consistent for (4-chlorophenyl)methyl borinic acid.

(4-Fluorophenyl)methylborinic acid (6n)

In a similar manner as for 6m, the titled compound was obtained from the reaction of 4-fluorophenylmagnesium bromide with di(isopropoxy)methylborane. The product was obtained by chromatography over silica gel.

(4-Biphenyl)methylborinic acid (6o)

In a similar manner as for 6m, the titled compound was obtained from the reaction of 4-biphenyllithium with di(isopropoxy)methylborane. The product was obtained by chromatography over silica gel.

(3-Chloro-4-methylphenyl)methylborinic acid (6p)

In a similar manner as for 6m, the titled compound was obtained from the reaction of 3-chloro-4-methylphenyl-lithium with di(isopropoxy)methylborane. The product was obtained by chromatography over silica gel.

(3-Chloro-4-methoxyphenyl)methylborinic acid (6q)

In a similar manner as for 6m, the titled compound was obtained from the reaction of 3-chloro-4-methoxyphenyl-lithium with di(isopropoxy)methylborane. The product was obtained by chromatography over silica gel.

(4-Dimethylaminophenyl)methylborinic acid (6r)

In a similar manner as for 6m, the titled compound was obtained from the reaction of 4-dimethylaminophenyllithium with di(isopropoxy)methylborane. The product was obtained by chromatography over silica gel.

(3-Pyridyl)vinyl borinic acid (6s)

Isopropylmagnesium chloride (2.0 M in THF) (5.0 mL, 10 mmol) was added to a solution of 3-bromopyridine (1.60 g, 10.0 mmol) in THF (15 mL) under nitrogen atmosphere at room temperature and the mixture was stirred for 1 h. Vinylboronic acid dibutyl ester (3.4 mL) was added to the reaction dropwise and the mixture was stirred at room temperature for 18 h. Water was added and the pH was adjusted to 7 with 1 M hydrochloric acid. The mixture was extracted with ethyl acetate. The organic layer was washed with brine and dried on anhydrous sodium sulfate. The solvent was removed under reduced pressure to give the title compound (1.04 g, 78%).

(3-Chloro-4-dimethylaminophenyl)vinylborinic acid (6t)

In a similar manner as for 6s, the titled compound was obtained from the reaction of 3-chloro-4-dimethylaminophenyllithium with vinylboronic acid dibutyl ester. The product was obtained by chromatography over silica gel.

Borinic Acid-Alkylalcohol Derivatives

Bis(3-Chlorophenyl)borinic acid 4-(hydroxyethyl)imidazole ester (121)

To a solution of bis(3-chlorophenyl)borinic acid (0.4 g, 1.428 mmol) in ethanol (10 ml), 4-(hydroxyethyl)imidazole hydrochloride (0.191 g, 1.428 mmol), sodium bicarbonate (0.180 g, 2.143 mmol) were added and the reaction mixture was stirred at room temperature for 18 h. Salt was removed by filtration. Filtrate was concentrated and treated with hexane to afford the product as a solid and was collected by filtration. (450 mg, 84.9% yield). $^1$H NMR (CD$_3$OD) δ (ppm) 2.92 (t, 2H), 3.82 (t, 2H), 7.0-7.2 (m, 9H), 7.90 (s, 1 H); (ES$^-$)(m/z) 343.11, MF C$_{17}$H$_{15}$BCl$_2$N$_2$O

Bis(4-Chlorophenyl)borinic acid 4-(hydroxymethyl)imidazole ester (126)

In a similar manner as in Example 121, the titled compound was obtained from the reaction of bis(4-chlorophenyl)borinic acid with 4-(hydroxymethyl)imidazole hydrochloride. The product was obtained as white crystals. (ES$^-$)(m/z) 328.79, MF C$_{16}$H$_{13}$BCl$_2$N$_2$O

Bis(3-Chloro-4-methylphenyl)borinic acid 1-benzyl-4-(hydroxymethyl)-imidazole ester (127)

To a solution of 1-benzyl-4-(hydroxymethyl)imidazole (96 mg, 0.521 mmol) in methanol (5 ml), bis(3-chloro-4-methylphenyl)borinic acid (121 mg, 0.521 mmol) was added and the reaction mixture was stirred at room temperature for 2 h. Solvent was removed under reduced pressure and the residue was treated with hexane to give a solid. The product was isolated by filtration and washed with hexane to give product (193 mg, 83%). $^1$H NMR (CDCl$_3$) δ: 2.3 (s, 6H, 2×CH$_3$), 4.8 (brs, 2H, CH$_2$), 5.1 (brs, 2H, CH$_2$), 6.9-7.4 (complex, 13H, Ar—H); MS (ES$^+$)(m/z) 448.78, MF C$_{25}$H$_{23}$BCl$_2$N$_2$O.

Bis(3-Chloro-4-methylphenyl)borinic acid 1-methyl-2-(hydroxymethyl)-imidazole ester (128)

In a similar manner as in Example 127, the titled compound was obtained from the reaction of bis(3-chloro-4-methylphenyl)borinic acid with 1-methyl-2-(hydroxy-methyl)imidazole hydrochloride. The product was obtained as white crystals. (ES$^+$)(m/z) 372.82, MF C$_{19}$H$_{21}$BCl$_2$N$_2$O

Bis(3-Chloro-4-methylphenyl)borinic acid 1-ethyl-2-(hydroxymethyl)-imidazole ester (129)

In a similar manner as in Example 127, the titled compound was obtained from the reaction of bis(3-chloro-4-methylphenyl)borinic acid with 1-ethyl-2-(hydroxy-methyl)imidazole hydrochloride. The product was obtained as white crystals. (ES$^+$)(m/z) 386.83, MF $C_{20}H_{23}BCl_2N_2O$

Bis(3-Chloro-4-methylphenyl)borinic acid 1-methyl-4-(hydroxymethyl)-imidazole ester (130)

In a similar manner as in Example 127, the titled compound was obtained from the reaction of bis(3-chloro-4-methylphenyl)borinic acid with 1-methyl-4-(hydroxy-methyl)imidazole hydrochloride. The product was obtained as white crystals. (ES$^+$)(m/z) 372.88, MF $C_{19}H_{21}BCl_2N_2O$

Bis(3-Chloro-4-methylphenyl)borinic acid 2-pyridylethanol (131)

In a similar manner as in Example 121, the titled compound was obtained from the reaction of bis(3-chloro-4-methylphenyl)borinic acid with 2-pyridylethanol. The product was obtained as white crystals. (ES$^+$)(m/z) 383.84, MF $C_{21}H_{20}BCl_2NO$ Hydroxyquinoline Derivatives

Bis(3-Chlorophenyl)borinic acid 5-cyano-8-hydroxyquinoline ester (19)

To a solution of bis(3-chlorophenyl)borinic acid (0.25 g) in ethanol (5 ml) and water (2 ml) was added 5-cyano-8-hydroxyquinoline (0.15 g). The solution was stirred at room temperature for 21 hours. A yellow solid precipitate formed which was collected by filtration and washed with cold ethanol. The product was obtained as yellow crystals. $^1$H NMR (DMSO-d6) δ (ppm) 7.24-7.35 (m, 8H), 7.38 (d, 1H), 8.18 (dd, 1H), 8.40 (d, 1H), 8.86 (d, 1H), 9.50 (d, 1H).

(3-Chlorophenyl)(2-thienyl)borinic acid 8-hydroxyquinoline ester (36)

To a solution of (3-chlorophenyl)(2-thienyl)borinic acid (1.5 g) in ethanol (2 ml) was added 8-hydroxyquinoline (0.77 g) in hot ethanol (2 ml). The reaction was heated to reflux and cooled to room temperature. A yellow solid precipitated. The mixture was cooled in ice, the solid was collected by filtration and washed with cold ethanol. The product was obtained as a yellow solid (1.01 g). $^1$H NMR (DMSO) δ (ppm) 6.98-7.06 (m, 2H), 7.19-7.26 (m, 3H), 7.38-7.50 (m, 4H), 7.71 (t, 1H), 7.91 (dd, 1H), 8.80 (d, 1H), 9.18 (d, 1H); (ESI$^+$)(m/z) 350.1, MF $C_{19}H_{13}BClNOS$

(2-Thienyl)methylborinic acid 8-hydroxyquinoline ester (26)

In a similar manner as in Example 36, the titled compound was obtained from the reaction of (2-thienyl)methylborinic acid with 8-hydroxyquinoline. The product was obtained as yellow crystals.

(3-Cyanophenyl)vinylborinic acid 8-hydroxyquinoline ester (40)

In a similar manner as in Example 36, the titled compound was obtained from the reaction of (3-cyanophenyl)vinylborinic acid with 8-hydroxyquinoline. The product was obtained as yellow crystals. (ESI$^+$)(m/z) 285.1, MF $C_{18}H_{13}BN_2O$

(2-Chlorophenyl)ethynylborinic acid 8-Hydroxyquinoline ester (43)

In a similar manner as in Example 36, the titled compound was obtained from the reaction of (2-chlorophenyl)ethynylborinic acid with 8-hydroxyquinoline. The product was obtained as yellow crystals. (ESI$^+$)(m/z) 292.1, MF $C_{17}H_{11}BClNO$

Bis(ethynyl)borinic acid 8-Hydroxyquinoline (44)

In a similar manner as in Example 36, the titled compound was obtained from the reaction of bis(ethynyl)borinic acid with 8-hydroxyquinoline. The product was obtained as light yellow crystals. (ESI$^+$)(m/z) 206.1, MF $C_{13}H_8BNO$

(3-Fluorophenyl)cyclopropylborinic acid 8-hydroxyquinoline ester (70)

In a similar manner as in Example 36, the titled compound was obtained from the reaction of (3-fluorophenyl)cyclopropylborinic acid with 8-hydroxyquinoline. The product was obtained as light yellow crystals. (ES$^-$)(m/z) 291.05, MF $C_{18}H_{15}BFNO$

(3-Pyridyl)vinylborinic acid 8-hydroxyquinoline ester (99)

A solution of (3-pyridyl)vinyl borinic acid (1.04 g, 7.82 mmol) and 8-hydroxyquinoline (961 mg, 6.63 mmol) in ethanol was stirred at 40° C. for 20 min. The solvent was removed under reduced pressure and the residue was crystallized from diethyl ether/diisopropyl ether/hexane to afford the title product (99) as a light yellow powder (355 mg, 21%). $^1$H NMR (DMSO-d$_6$) δ (ppm) 5.23 (dd, 1H), 5.46 (dd, 1H), 6.43 (dd, 1H), 7.14 (d, 1H), 7.19 (dd, 1H), 7.41 (d, 1H), 7.6-7.8 (m, 2H), 7.88 (dd, 1H), 8.35 (dd, 1H), 8.57 (s, 1H), 8.76 (d, 1H), 9.00 (d, 1H); ESI$^+$ (m/z) 261 MF $C_{16}H_{13}BN_2O$.

(4-(Dimethylaminomethyl)phenyl)(3-fluorophenyl) borinic acid 8-hydroxy-quinoline ester (100)

In a similar manner as in Example 99, the titled compound was obtained from the reaction of (4-(Dimethylaminomethyl) phenyl)(3-fluorophenyl)borinic acid with 8-hydroxyquinoline. The product was obtained as a light yellow powder. ESI$^+$ (m/z) 385 MF $C_{24}H_{22}BFN_2O$.

3-Hydroxypicolinic Acid Derivatives

Bis(3-Chloro-4-methylphenyl)borinic acid 3-hydroxypicolinate ester (111)

Bis(3-chloro-4-methylphenyl)borinic acid (14.6 g) was dissolved in ethanol (120 ml) and heated to reflux. 3-Hydroxypicolinic acid (5.83 g) was added in portions to the hot solution. The reaction was stirred at reflux for 15 minutes after the addition of the last portion of 3-hydroxypicolinic acid was added and then cooled to room temperature. Reaction was concentrated by removal of some ethanol. Solid was removed by filtration. One recrystallization from ethanol afforded the title product as white crystals (13.4 g). MP=165.0-166.5° C.

In a preferred embodiment, the present invention includes the compounds specifically recited herein, and pharmaceutically acceptable salts thereof, and compositions of any of these compounds where these comprise a pharmaceutically acceptable carrier.

The present invention also relates to a method for treating a microbial-caused disease in a patient afflicted therewith and/or preventing such infection in a patient at risk of becoming so-infected, comprising administering to said patient a therapeutically effective amount of any of the compounds of the invention, preferably one or more of those listed in Tables 1 to 4. In one aspect, the compounds of the invention have anti-bacterial (i.e., bactericidal) and anti-fungal (i.e., fungicidal) activity.

In a preferred embodiment, the microbe is a bacterium, preferably a gram positive bacterium, wherein said gram positive bacterium is a member selected from the group consisting of *Staphylococcus* species, *Streptococcus* species, *Bacillus* species, *Mycobacterium* species, *Corynebacterium* species, *Clostridium* species, *Actinomyces* species, *Enterococcus* species, and *Streptomyces* species.

In another preferred embodiment of such method, the bacterium is a gram negative bacterium, preferably one selected from the group consisting of *Acinetobacter* species, *Neisseria* species, *Pseudomonas* species, *Brucella* species, *Agrobacterium* species, *Bordetella* species, *Escherichia* species, *Shigella* species, *Yersinia* species, *Salmonella* species, *Klebsiella* species, *Enterobacter* species, *Haemophilus* species, *Pasteurella* species, *Streptobacillus* species, *spirochetal* species, *Campylobacter* species, *Vibrio* species, and *Helicobacter* species.

In a highly preferred embodiment of the present invention, the bacterium is a member selected from the group consisting of *Staphylococcus aureus*; *Staphylococcus epidermidis*; *Staphylococcus saprophyticus*; *Streptococcus pyogenes*; *Streptococcus agalactiae*; *Streptococcus pneumoniae*; *Enterococcus faecalis*; *Enterococcus faecium*; *Bacillus anthracis*; *Mycobacterium avium*; *Mycobacterium tuberculosis*; *Acinetobacter baumanii*; *Corynebacterium diphtheria*; *Clostridium perfringens*; *Clostridium botulinum*; *Clostridium tetani*; *Neisseria gonorrhoeae*; *Neisseria meningitidis*; *Pseudomonas aeruginosa*; *Legionella pneumophila*; *Escherichia coli*; *Yersinia pestis*; *Haemophilus influenzae*; *Helicobacter pylori*; *Campylobacter fetus*; *Campylobacter jejuni*; *Vibrio cholerae*; *Vibrio parahemolyticus*; *Trepomena pallidum*; *Actinomyces israelii*; *Rickettsia prowazekii*; *Rickettsia rickettsii*; *Chlamydia trachomatis*; *Chlamydia psittaci*; *Brucella abortus*; *Agrobacterium tumefaciens*; and *Francisella tularensis*.

In a preferred embodiment the microbe is a fungus or yeast wherein said fungus is a member selected from the group consisting of *Aspergillus* species, *Trichophyton* species, *Microsporium* species, *Cryptococcus neoformans*, *Blastomyces dermatitidis*, *Coccidiodes immitis*, *Histoplasma capsulatum*, or *Paracoccidioides brasiliensis* and wherein said yeast is a member selected from the group consisting of *Candida albicans*, *Candida glabrata*, *Candida krusei*, *Candida tropicalis*, or *Candida parapsilosis*.

What is claimed is:

1. A compound which is a member selected from:
a chemical compound having a structure of the following Formula:

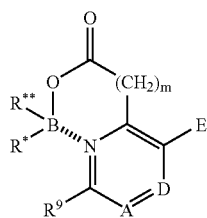

Formula wherein B is boron, O is oxygen wherein R* and R** are each independently selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted phenyl, and substituted or unsubstituted heterocycle, with the proviso that one of R* and R** is a substituted or unsubstituted alkyl ($C_1$-$C_4$), and wherein A is CH, $CR^{10}$ or N, and wherein D is N, CH, or $CR^{12}$, and wherein E is OH, alkoxy or 2-(morpholino)ethoxy, $CO_2H$ or $CO_2$alkyl and wherein m=0-2, wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$, and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH, and salts of said chemical compound having a structure of said Formula.

2. A compound which is a member selected from:
a chemical compound having a structure of the following Formula:

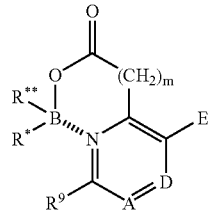

Formula wherein B is boron, O is oxygen wherein R* and R** are each a substituted or unsubstituted alkyl ($C_1$-$C_4$)

and wherein A is CH, $CR^{10}$ or N, and wherein D is N, CH, or $CR^{12}$ and wherein E is OH, alkoxy or 2-(morpholino)ethoxy, $CO_2H$ or $CO_2$alkyl and wherein m=0-2, wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$, and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$-alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH, and salts of said chemical compound having a structure of said Formula.

3. A compound which is a member selected from:
a chemical compound having a structure of the following Formula:

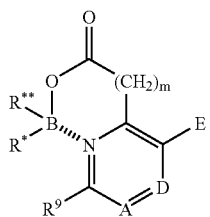

Formula wherein B is boron, O is oxygen
wherein one of R* and R** is a substituted or unsubstituted cycloalkyl ($C_3$-$C_7$),
and wherein A is CH, $CR^{10}$ or N,
and wherein D is N, CH, or $CR^{12}$,
and wherein E is OH, alkoxy or 2-(morpholino)ethoxy, $CO_2H$ or $CO_2$alkyl
and wherein m=0-2,
wherein $R^{12}$ is selected from $(CH_2)_k OH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_n OH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

4. A compound which is a member selected from:
a chemical compound having a structure of the following Formula:

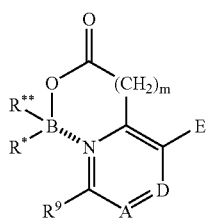

Formula wherein B is boron, O is oxygen
wherein R* and R** are each a substituted or unsubstituted cycloalkyl ($C_3$-$C_7$),
and wherein A is CH, $CR^{10}$ or N,
and wherein D is N, CH, or $CR^{12}$,
and wherein E is OH, alkoxy or 2-(morpholino)ethoxy, $CO_2H$ or $CO_2$alkyl
and wherein m=0-2,
wherein $R^{12}$ is selected from $(CH_2)_k OH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_{12}$,
and wherein $R^9$ and $R^{10}$ are members independently selected from the group consisting of hydrogen, alkyl, cycloalkyl, $(CH_2)_n OH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

5. A compound which is a member selected from:
a chemical compound having a structure of the following Formula:

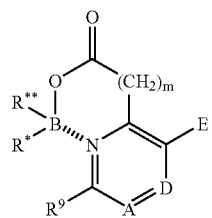

Formula wherein B is boron, O is oxygen
wherein one of R* and R** is a substituted or unsubstituted alkenyl,
and wherein A is CH, $CR^{10}$ or N,
and wherein D is N, CH, or $CR^{12}$,
and wherein E is OH, alkoxy or 2-(morpholino)ethoxy, $CO_2H$ or $CO_2$alkyl
and wherein m=0-2,
wherein $R^{12}$ is selected from $(CH_2)_k OH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_n OH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

6. A compound which is a member selected from:
a chemical compound having a structure of the following Formula:

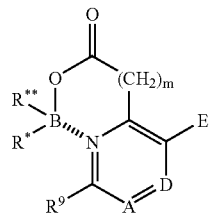

Formula wherein B is boron, O is oxygen
wherein R* and R** are each a substituted or unsubstituted alkenyl,
and wherein A is CH, $CR^{10}$ or N,
and wherein D is N, CH, or $CR^{12}$, and wherein E is OH, alkoxy or 2-(morpholino)ethoxy, $CO_2H$ or $CO_2$alkyl
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

7. The compound of claim 5 or 6 wherein said alkenyl has the structure:

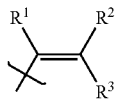

wherein $R^1$, $R^2$, and $R^3$ are each independently selected from the group consisting of hydrogen, alkyl, cycloalkyl, aryl, substituted aryl, aralkyl, substituted aralkyl, $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$ and $NO_2$.

8. A compound which is a member selected from:
a chemical compound having a structure of the following Formula:

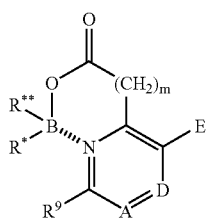

wherein B is boron, O is oxygen
wherein one of R* and R** is a substituted or unsubstituted alkynyl,
and wherein A is CH, $CR^{10}$ or N,
and wherein D is N, CH, or $CR^{12}$,
and wherein E is OH, alkoxy or 2-(morpholino)ethoxy, $CO_2H$ or $CO_2$alkyl
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

9. A compound which is a member selected from:
a chemical compound having a structure of the following Formula:

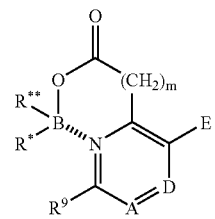

wherein B is boron, O is oxygen
wherein R* and R** are each a substituted or unsubstituted alkynyl,
and wherein A is CH, $CR^{10}$ or N,
and wherein D is N, CH, or $CR^{12}$,
and wherein E is OH, alkoxy or 2-(morpholino)ethoxy, $CO_2H$ or $CO_2$alkyl
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$-alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

10. The compound of claim 8 or 9 wherein said alkynyl has the structure:

wherein $R^1$ is selected from the group consisting of hydrogen, alkyl, cycloalkyl, aryl, substituted aryl, aralkyl, substituted aralkyl, $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$ and $NO_2$.

11. A compound which is a member selected from:
a chemical compound having a structure of the following Formula:

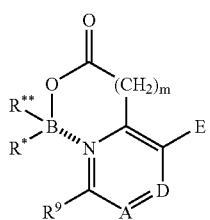

wherein B is boron, O is oxygen
wherein R* and R** are each independently selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted phenyl, and substituted or unsubstituted heterocycle, with the proviso that one of R* or R** is benzyl or substituted benzyl,
and wherein A is CH, $CR^{10}$ or N,
and wherein D is N, CH, or $CR^{12}$,
and wherein E is OH, alkoxy or 2-(morpholino)ethoxy, $CO_2H$ or $CO_2$alkyl
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

12. A compound which is a member selected from:
a chemical compound having a structure of the following Formula:

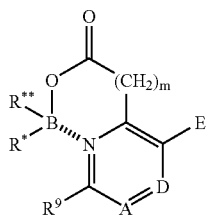

wherein B is boron, O is oxygen
wherein R* and R** are each a substituted or unsubstituted cycloalkyl ($C_3$-$C_7$),
and wherein A is CH, $CR^{10}$ or N,
and wherein D is N, CH, or $CR^{12}$,
and wherein E is N-(morpholinyl)ethoxy or alkoxy greater than $C_4$
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

13. A compound which is a member selected from:
a chemical compound having a structure of the following Formula:

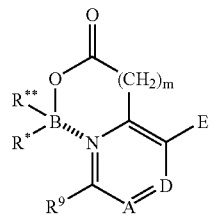

wherein B is boron, O is oxygen
wherein R* and R** are each a substituted or unsubstituted cycloalkyl ($C_3$-$C_7$),
and wherein A is N,
and wherein D is N,
and wherein E is OH, alkoxy or 2-(morpholino)ethoxy, $CO_2H$ or $CO_2$alkyl
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

14. A compound which is a member selected from:
a chemical compound having a structure of the following Formula:

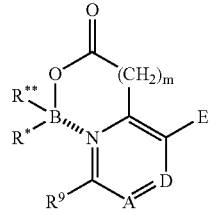

wherein B is boron, O is oxygen
wherein R* and R** are each 3-chloro-4-methylphenyl, $R^9$ is H, A is CH, D is CH, E is OH, and m=0,
and salts of said chemical compound having a structure of said Formula.

15. A compound which is a member selected from:
a chemical compound having a structure of the following Formula:

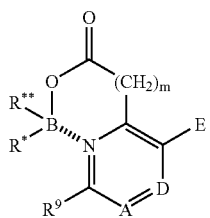

Formula wherein B is boron, O is oxygen
wherein R* and R** are each 2-methyl-4-chlorophenyl, $R^9$ is H, A is CH, D is CH, E is OH, and m=0
and salts of said chemical compound having a structure of said Formula.

16. A compound which is a member selected from:
a chemical compound having a structure of the following Formula:

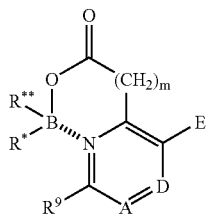

Formula wherein B is boron, O is oxygen
wherein R* and R** are each independently selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted phenyl, and substituted or unsubstituted heterocycle, with the proviso that one of R* and R** is a substituted or unsubstituted aralkyl,
and wherein A is CH, $CR^{10}$ or N,
and wherein D is N, CH, or $CR^{12}$,
and wherein E is OH, alkoxy or 2-(morpholino)ethoxy, $CO_2H$ or $CO_2$alkyl
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3-amino, $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

17. A compound which is a member selected from:
a chemical compound having a structure of the following Formula:

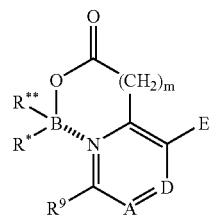

Formula wherein B is boron, O is oxygen
wherein R* and R** are each a substituted or unsubstituted aralkyl,
and wherein A is CH, $CR^{10}$ or N,
and wherein D is N, CH, or $CR^{12}$,
and wherein E is OH, alkoxy or 2-(morpholino)ethoxy, $CO_2H$ or $CO_2$alkyl
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3$ H and OH,
and salts of said chemical compound having a structure of said Formula.

18. The compound of claim 16 or 17 wherein said aralkyl is benzyl and has the structure:

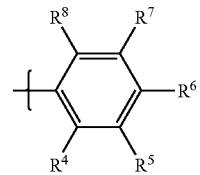

wherein $R^4$, $R^5$, $R^6$, $R^7$ and $R^8$ are each independently selected from the group consisting of alkyl, cycloalkyl, aryl, substituted aryl, aralkyl, substituted aralkyl, $(CH_2)_k$OH (where k=1, 2 or 3), $CH_2NH_2$, $CH_2NH$-alkyl, $CH_2N(alkyl)_2$, $CO_2H$, $CO_2$alkyl, $CONH_2$, $CONH$alkyl, $CON(alkyl)_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, $2^o$-amino, $3^o$-amino, $NH_2SO_2$, $OCH_2CH_2NH_2$, $OCH_2CH_2NH$alkyl, $OCH_2CH_2N(alkyl)_2$, oxazolidin-2-yl, and alkyl substituted oxazolid in-2-yl.

19. A compound which is a member selected from:
a chemical compound having a structure of the following Formula:

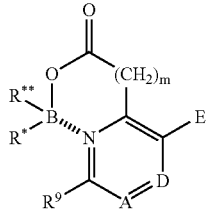

Formula wherein B is boron, O is oxygen
wherein one of R* and R** is a substituted or unsubstituted heterocycle
and wherein A is CH, $CR^{10}$ or N,
and wherein D is N, CH, or $CR^{12}$,
and wherein E is OH, alkoxy or 2-(morpholino)ethoxy, $CO_2H$ or $CO_2$alkyl
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, CO2-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

20. A compound which is a member selected from:
a chemical compound having a structure of the following Formula:

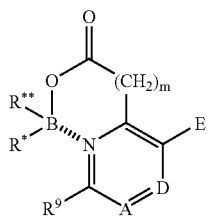

Formula wherein B is boron, O is oxygen
wherein R* and R** are each a substituted or unsubstituted heterocycle,
and wherein A is CH, $CR^{10}$ or N,
and wherein D is N, CH, or $CR^{12}$,
and wherein E is OH, alkoxy or 2-(morpholino)ethoxy, $CO_2H$ or $CO_2$alkyl
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, CO2-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

21. The compound of claim 19 and 20 wherein said heterocycle has the structure

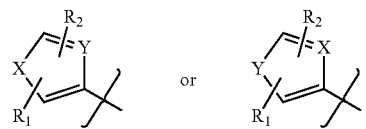

wherein X=CH=CH, N=CH, $NR^{13}$ (wherein $R^{13}$=H, alkyl, aryl or aralkyl), O, or S
and wherein Y=CH or N
and wherein $R^1$, $R^2$, and $R^3$ are each independently selected from the group consisting of hydrogen, alkyl, cycloalkyl, aryl, substituted aryl, aralkyl, substituted aralkyl, $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, S-alkyl, S-aryl, $SO_2$alkyl, $SO_2N(alkyl)_2$, $SO_2NH$alkyl, $SO_2NH_2$, $SO_3$=H, $SCF_3$, CN, halogen, $CF_3$, $NO_2$, oxazolidin-2-yl, or alkyl substituted oxazolidin-2-yl.

22. A compound which is a member selected from:
a chemical compound having a structure of the following Formula:

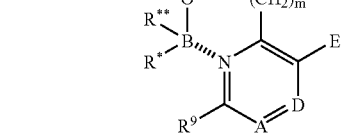

Formula wherein B is boron, O is oxygen
wherein R* and R** are each independently selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted phenyl, and substituted or unsubstituted heterocycle,
and wherein A is CH,
and wherein D is CH,
and wherein E is OH,
and wherein m=0,
and wherein $R^9$ is H,
and salts of said chemical compound having a structure of said Formula.

23. A solvent adduct having the structure:

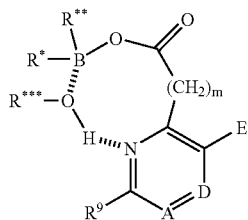

Formula wherein B is boron, O is oxygen
wherein R* and R** are each independently selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted phenyl, and substituted or unsubstituted heterocycle,
and wherein A is CH, $CR^{10}$ or N,
and wherein D is N, CH, or $CR^{12}$,
and wherein E is OH, alkoxy or 2-(morpholino)ethoxy, $CO_2H$ or $CO_2$alkyl
and wherein m=0-2,
wherein $R^{12}$ is selected from $(CH_2)_k OH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3-amino, $NH_2SO_2$ and $CONH_2$,
and wherein $R^9$ and $R^{10}$ are members independently selected from the group consisting of hydrogen, alkyl, cycloalkyl, $(CH_2)_n OH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and wherein R*** is H or alkyl
and salts of said chemical compound having a structure of said Formula.

24. A compound which is a member selected from:

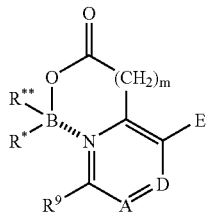

Formula a chemical compound having the structure of the following Formula:
wherein B is boron, O is oxygen
wherein R* and R** are the same and are members selected from substituted or unsubstituted alkyl ($C_1$-$C_4$),
and wherein A is CH, $CR^{10}$ or N,
and wherein D is N, CH, or $CR^{12}$,
and wherein E is H, OH, alkoxy or 2-(morpholino)ethoxy, $CO_2H$ or $CO_2$alkyl
and wherein m=0-2,
wherein $R^{12}$ is selected from $(CH_2)_k OH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_n OH$ (n 1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

25. A compound which is a member selected from:
a chemical compound having the structure of the following Formula:

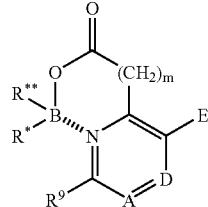

Formula wherein B is boron, O is oxygen
wherein R* and R** are the same and are members selected from substituted or unsubstituted cycloalkyl ($C_3$-$C_7$),
and wherein A is CH, $CR^{10}$ or N,
and wherein D is N, CH, or $CR^{12}$,
and wherein E is H, OH, alkoxy or 2-(morpholino)ethoxy, $CO_2H$ or $CO_2$alkyl
and wherein m=0-2,
wherein $R^{12}$ is selected from $(CH_2)_k OH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_n OH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

26. A compound which is a member selected from:
a chemical compound having the structure of the following Formula:

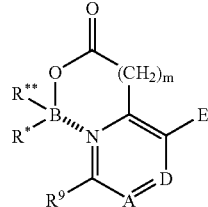

Formula wherein B is boron, O is oxygen
wherein R* and R** are the same and are members selected from substituted or unsubstituted alkenyl,
and wherein A is CH, $CR^{10}$ or N,
and wherein D is N, CH, or $CR^{12}$,
and wherein E is H, OH, alkoxy or 2-(morpholino)ethoxy, $CO_2H$ or $CO_2$alkyl
and wherein m=0-2, wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$, and wherein $R^{9}$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH, and salts of said chemical compound having a structure of said Formula.

27. The compound of claim 26 wherein said alkenyl has the structure:

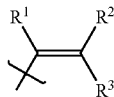

wherein $R^1$, $R^2$, and $R^3$ are each independently selected from the group consisting of hydrogen, alkyl, cycloalkyl, aryl, substituted aryl, aralkyl, substituted aralkyl, $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$ and $NO_2$.

28. A compound which is a member selected from:
a chemical compound having the structure of the following Formula:

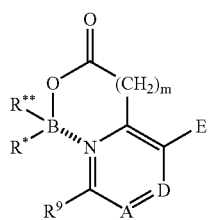

Formula wherein B is boron, O is oxygen
wherein R* and R** are the same and are members selected from substituted or unsubstituted alkenyl and substituted or unsubstituted alkynyl,
and wherein A is CH, $CR^{10}$ or N,
and wherein D is N, CH, or $CR^{12}$,
and wherein E is H, OH, alkoxy or 2-(morpholino)ethoxy, $CO_2H$ or $CO_2$alkyl
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^{9}$ and $R^{10}$ are members independently selected from the group consisting of hydrogen, alkyl, cycloalkyl, $(CH_2)_nOH$ (n=1 to 3), $CH_2NH_2$, $CH_2NH$-alkyl, $CH_2N(alkyl)_2$, halogen, CHO, CH=NOH, $CO_2H$, $CO_2H$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH, and salts of said chemical compound having a structure of said Formula.

29. The compound of claim 28, wherein said alkynyl has the structure:

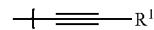

wherein $R^1$ is selected from the group consisting of hydrogen, alkyl, cycloalkyl, aryl, substituted aryl, aralkyl, substituted aralkyl, $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$ and $NO_2$.
and wherein A is CH, $CR^{10}$ or N,
and wherein D is N, CH, or $CR^{12}$,
and wherein E is H, OH, alkoxy or 2-(morpholino)ethoxy, $CO_2H$ or $CO_2$alkyl and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^{9}$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

30. A compound which is a member selected from:
a chemical compound having the structure of the following Formula:

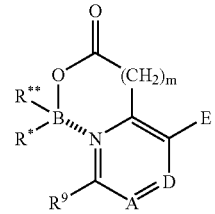

Formula wherein B is boron, O is oxygen
wherein R* and R** are the same and are members selected from substituted or unsubstituted phenyl
and wherein A is CH, $CR^{10}$ or N,
and wherein D is N, CH, or $CR^{12}$,
and wherein E is OH, alkoxy or 2-(morpholino)ethoxy, $CO_2H$ or $CO_2$alkyl
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^{9}$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NHalkyl$, $SO_2NH_2$, $NH_2$, alkoxy, $CF_3$, $SCF_3$, $NO_2$, $SO_3H$ and OH, and salts of said chemical compound having a structure of said Formula.

31. A compound which is a member selected from:

a chemical compound having the structure of the following Formula:

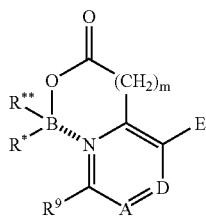

Formula wherein B is boron, O is oxygen wherein R* and R** are the same and are members selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted phenyl, and substituted or unsubstituted heterocycle, and wherein R* and R** are other than a phenyl or substituted phenyl, and wherein A is CH, $CR^{10}$ or N, and wherein D is N, CH, or $CR^{12}$, and wherein B is H, OH, alkoxy or 2-(morpholino)ethoxy, $CO_2H$ or $CO_2alkyl$ and wherein m=0-2, wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2alkyl$, $CONH_2$, OH, alkoxy, aryloxy, SH, S-alkyl, S-aryl, $SO_2alkyl$, $SO_2N(alkyl)_2$, $SO_2NHalkyl$, $SO_2NH_2$, $SO_3H$, $SCF_3$, CN, halogen, $CF_3$, $NO_2$, $NH_2$, 2*-amino, 3*-amino, $NH_2SO_2$ and $CONH_2$, and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NHalkyl$, $CH_2N(alkyl)_2$, halogen, CHO, CH=NOH, $CO_2H$, $CO_2$-alkyl, S-alkyl, $SO_2$-alkyl, S-aryl, $SO_2N(alkyl)_2$, $SO_2NHalkyl$, $SO_2NH_2$, $NH_2$, alkoxy, $CF_3$, $SCF_3$, $NO_2$, $SO_3H$ and OH, and salts of said chemical compound having a structure of said Formula.

32. A compound which is a member selected from:

a chemical compound having the structure of the following Formula:

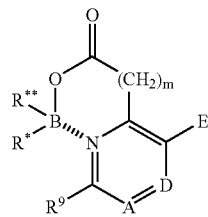

Formula wherein B is boron, O is oxygen wherein R* and R** are the same and are members selected from benzyl and substituted benzyl, and wherein A is CH, $CR^{10}$ or N, and wherein D is N, CH, or $CR^{12}$, and wherein E is H, OH, alkoxy or 2-(morpholino)ethoxy, $CO_2H$ or $CO_2alkyl$ and wherein m=0-2, wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2alkyl$, $CONH_2$, OH, alkoxy, aryloxy, SH, S-alkyl, S-aryl, $SO_2alkyl$, $SO_2N(alkyl)_2$, $SO_2NHalkyl$, $SO_2NH_2$, $SO_3H$, $SCF_3$, CN, halogen, $CF_3$, $NO_2$, $NH_2$, 2*-amino, 3*-amino, $NH_2SO_2$ and $CONH_2$, and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NHalkyl$, $CH_2N(alkyl)_2$, halogen, CHO, CH=NOH, $CO_2H$, C02-alkyl, S-alkyl, $SO_2alkyl$, S-aryl, $SO_2N(alkyl)_2$, $SO_2NHalkyl$, $SO_2NH_2$, $NH_2$, alkoxy, $CF_3$, $SCF_3$, $NO_2$, $SO_3H$ and OH, and salts of said chemical compound having a structure of said Formula.

33. A compound which is a member selected from:

a chemical compound having the structure of the following Formula:

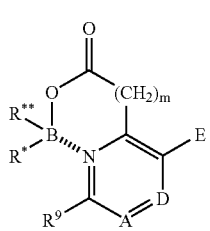

Formula wherein B is boron, O is oxygen wherein R* and R** are the same and are members selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted phenyl, and substituted or unsubstituted heterocycle, and wherein A is CH, $CR^{10}$ or N, and wherein D is N, CH, or $CR^{12}$, and wherein E is OH and wherein m=0, wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2alkyl$, $CONH_2$, OH, alkoxy, aryloxy, SH, S-alkyl, S-aryl, $SO_2alkyl$, $SO_2N(alkyl)_2$, $SO_2NHalkyl$, $SO_2NH_2$, $SO_3H$, $SCF_3$, CN, halogen, $CF_3$, $NO_2$, $NH_2$, 2*-amino, 3*-amino, $NH_2SO_2$ and $CONH_2$, and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NHalkyl$, $CH_2N(alkyl)_2$, halogen, CHO, CH=NOH, $CO_2H$, $CO_2$-alkyl, S-alkyl, $SO_2alkyl$, S-aryl, $SO_2N(alkyl)_2$, $SO_2NHalkyl$, $SO_2NH_2$, $NH_2$, alkoxy, $CF_3$, $SCF_3$, $NO_2$, $SO_3H$ and OH, and salts of said chemical compound having a structure of said Formula.

34. A compound which is a member selected from:

a chemical compound having the structure of the following Formula:

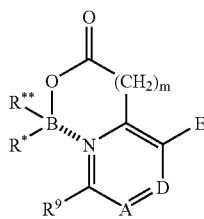

Formula wherein B is boron, O is oxygen
wherein R* and R** are the same and are members selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted phenyl, and substituted or unsubstituted heterocycle,
and wherein A is CH, $CR^{10}$ or N,
and wherein D is N, CH, or $CR^{12}$,
and wherein E is OH, alkoxy or 2-(morpholino)ethoxy, $CO_2H$ or $CO_2$alkyl
and wherein m=0-2,
wherein $R^{12}$ is selected from $(CH_2)_k OH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ is a member selected from the group consisting of hydrogen, alkyl, cycloalkyl, $(CH_2)_n OH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
$R^{10}$ is selected from alkyl (greater than $C_4$), $(CH_2)_k OH$ (n=1, 2 or 3), $CH_2NH_2$, $CH_2NH$alkyl, $CH_2N(alkyl)_2$, CHO, CH=NOH, $CO_2H$, $CO_2$-alkyl, S-alkyl, $SO_2$-alkyl, S-aryl, alkoxy (greater than $C_4$), $SCF_3$ and $NO_2$
and salts of said chemical compound having a structure of said Formula.

35. A compound which is a member selected from:
a chemical compound having the structure of the following Formula:

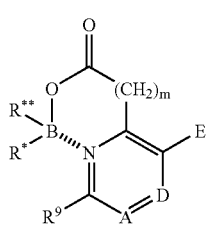

Formula wherein B is boron, O is oxygen
wherein R* and R** are the same and are members selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted phenyl, and substituted or unsubstituted heterocycle,
and wherein A is CH, $CR^{10}$ or N,
and wherein D is $CR^{12}$,
and wherein E is H, OH, alkoxy or 2-(morpholino)ethoxy, $CO_2H$ or $CO_2$alkyl and wherein m=0-2,
wherein $R^{12}$ is selected from $(CH_2)_k OH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy (greater than $C_4$), aryloxy, SH, S-alkyl, S-aryl, $SO_2$alkyl, $SO_3H$, $SCF_3$, CN, $NO_2$, $NH_2SO_2$ and $CONH_2$,
and wherein $R^9$ and $R^{10}$ are members independently selected from the group consisting of hydrogen, alkyl, cycloalkyl, $(CH_2)_n OH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

36. A compound which is a member selected from:
a chemical compound having the structure of the following Formula:

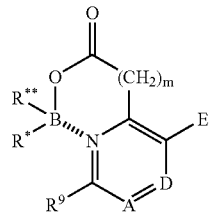

Formula wherein B is boron, O is oxygen
wherein R* and R** are the same and are members selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted phenyl, and substituted or unsubstituted heterocycle,
and wherein A is CH, $CR^{10}$ or N,
and wherein D is N, CH, or $CR^{12}$,
and wherein E is N-(morpholinyl)ethoxy or alkoxy greater than $C_4$
and wherein m=0-2,
wherein $R^{12}$ is selected from $(CH_2)_k OH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_n OH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$
and OH,
and salts of said chemical compound having a structure of said Formula.

37. A compound which is a member selected from:
a chemical compound having the structure of the following Formula:

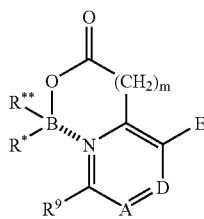

wherein B is boron, O is oxygen
wherein R* and R** are the same and are members selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted phenyl, and substituted or unsubstituted heterocycle,
and wherein A is CH, $CR^{10}$ or N,
and wherein D is N, CH, or $CR^{12}$,
and wherein E is H, OH, alkoxy or 2-(morpholino)ethoxy, $CO_2H$ or $CO_2$alkyl
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
wherein A or D is nitrogen
and salts of said chemical compound having a structure of said Formula.

38. A compound which is a member selected from:
a chemical compound having the structure of the following Formula:

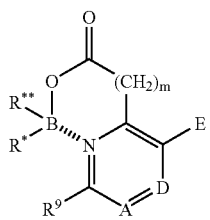

wherein B is boron, O is oxygen
wherein R* and R** are the same and are members selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted phenyl, and substituted or unsubstituted heterocycle,
and wherein A is CH, $CR^{10}$ or N,
and wherein D is N, CH, or $CR^{12}$,
and wherein E is H, OH, alkoxy or 2-(morpholino)ethoxy, $CO_2H$ or $CO_2$alkyl
and wherein m=2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$
and OH,
and salts of said chemical compound having a structure of said Formula.

39. A compound which is a member selected from:
a chemical compound having the structure of the following Formula:

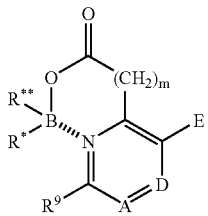

wherein B is boron, O is oxygen
wherein R* and R** are the same and are members selected from substituted phenyl substituted with 1 to 5 substituents each of which is independently selected from alkyl (greater than $C_6$), aryl, substituted aryl, benzyl, substituted benzyl, $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, $CONH$alkyl, $CON(alkyl)_2$, OH, alkoxy (greater than $C_6$), aryloxy, SH, S-alkyl, S-aryl, $SO_2$alkyl, $SO_3H$, $SCF_3$, CN, NO2, $NH_2$, 2°-amino, 3°-amino, $NH_2SO_2$, $OCH_2CH_2NH_2$, $OCH_2CH_2NH$alkyl, $OCH_2CH_2N(alkyl)_2$, oxazolidin-2-yl and alkyl substituted oxazolidin-2-yl,
and wherein A is CH, $CR^{10}$ or N,
and wherein D is N, CH, or $CR^{12}$,
and wherein E is H, OH, alkoxy or 2-(morpholino)ethoxy, $CO_2H$ or $CO_2$alkyl
and wherein m=0-2,
wherein $R_{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

40. The compound of claim 30 wherein said phenyl has the structure

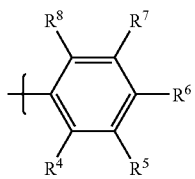

wherein $R^4$, $R^5$, $R^6$, $R^7$ and $R^8$ are each independently selected from the group consisting of hydrogen, alkyl, cycloalkyl, aryl, substituted aryl, aralkyl, substituted aralkyl, $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, CONHalkyl, $CON(alkyl)_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2°-amino, 3°-amino, $NH_2SO_2$, $OCH_2CH_2NH_2$, $OCH2CH_2NH$alkyl, $OCH_2CH_2N(alkyl)_2$, oxazolidin-2-yl, or alkyl substituted oxazolidin-2-yl.

41. A compound which is a member selected from:
a chemical compound having the structure of the following Formula:

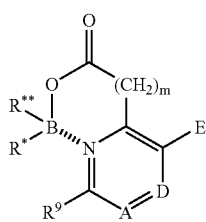

Formula wherein B is boron, O is oxygen
wherein R* and R** are each 3-chloro-4-methylphenyl,
and wherein and A is CH,
and wherein D is CH,
and wherein E is OH
and wherein m=0,
and wherein $R^9$ is H,
and salts of said chemical compound having a structure of said Formula.

42. A compound which is a member selected from:
a chemical compound having the structure of the following Formula:

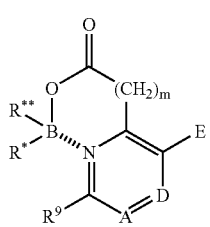

Formula wherein B is boron, O is oxygen
wherein R* and R** are each 2-methyl-4-chlorophenyl,
and wherein A is CH,
and wherein D is CH,
and wherein E is OH,
and wherein m=0,
and wherein $R^9$ H,
and salts of said chemical compound having a structure of said Formula.

43. A compound which is a member selected from:
a chemical compound having the structure of the following Formula:

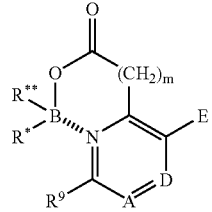

Formula wherein B is boron, O is oxygen
wherein R* and R** are the same and are members selected from substituted or unsubstituted aralkyl,
and wherein A is CH, $CR^{10}$ or N,
and wherein D is N, CH, or $CR^{12}$,
and wherein E is H, OH, alkoxy or 2-(morpholino)ethoxy, $CO_2H$ or $CO_2$alkyl
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, CO2-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

44. The compound of claim 43 wherein said aralkyl is benzyl and has the structure

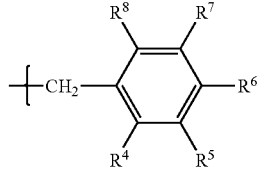

wherein $R^4$, $R^5$, $R^6$, $R^7$ and $R^8$ are each independently selected from the group consisting of alkyl, cycloalkyl, aryl, substituted aryl, aralkyl, substituted aralkyl, $(CH_2)_k$OH (where k=1, 2 or 3), $CH_2NH_2$, $CH_2NH$-alkyl, $CH_2N(alkyl)_2$, $CO_2H$, $CO_2$alkyl, $CONH_2$, CONHalkyl, $CON(alkyl)_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2°-amino, 3°-amino, $NH_2SO_2$, $OCH_2CH_2NH_2$, $OCH2CH_2NH$alkyl, $OCH_2CH_2N(alkyl)_2$, oxazolidin-2-yl, and alkyl substituted oxazolid in-2-yl.

45. A compound which is a member selected from:
a chemical compound having the structure of the following Formula:

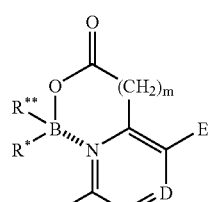

Formula wherein B is boron, O is oxygen
wherein R* and R** are the same and are members selected from substituted or unsubstituted heterocycle,
and wherein A is CH, $CR^{10}$ or N,
and wherein D is N, CH, or $CR^{12}$,
and wherein E is H, OH, alkoxy or 2-(morpholino)ethoxy, $CO_2H$ or $CO_2alkyl$
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2alkyl$, $CONH_2$, OH, alkoxy, aryloxy, SH, S-alkyl, S-aryl, $SO_2alkyl$, $SO_2N(alkyl)_2$, $SO_2NHalkyl$, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NHalkyl$, $CH_2N(alkyl)_2$, halogen, CHO, CH=NOH, $CO_2H$, $CO_2$-alkyl, S-alkyl, $SO_2alkyl$, S-aryl, $SO_2N(alkyl)_2$, $SO_2NHalkyl$, $SO_2NH_2$, $NH_2$, alkoxy, $CF_3$, $SCF_3$, $NO_2$, $SO_3H$ and OH,
and salts of said chemical compound having a structure of said Formula.

46. The compound of claim 45 wherein said heterocycle has the structure

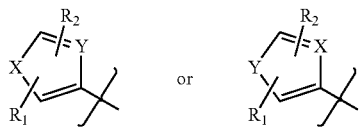

wherein X=CH=CH, N=CH, $NR^{13}$ (wherein $R^{13}$=H, alkyl, aryl or aralkyl), O, or S
and wherein Y=CH or N
and wherein $R^1$, $R^2$, and $R^3$ are each independently selected from the group consisting of hydrogen, alkyl, cycloalkyl, aryl, substituted aryl, aralkyl, substituted aralkyl, $(CH_2)_kOH$ (where k=1, 2 or 3), $CH_2NH_2$, $CH_2NH$-alkyl, $CH_2N(alkyl)_2$, $CO_2H$, $CO_2alkyl$, $CONH_2$, S-alkyl, S-aryl, $SO_2alkyl$, $SO_2N(alkyl)_2$, $SO_2NHalkyl$, $SO_2NH_2$, $SO_3$=H, $SCF_3$, CN, halogen, $CF_3$, $NO_2$, oxazolidin-2-yl and alkyl substituted oxazolidin-2-yl.

47. A compound which is a member selected from:
a chemical compound having the structure of the following Formula:

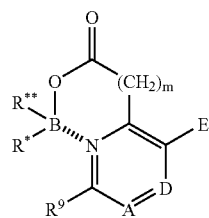

wherein B is boron, O is oxygen
wherein R* and R** are the same and are members selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted phenyl, and substituted or unsubstituted heterocycle,
and wherein D is A is CH,
and wherein D is CH,
and wherein E is OH,
and wherein m=0,
and wherein $R^9$ is H,
and salts of said chemical compound having a structure of said Formula.

48. A compound which is a member selected from:
a solvent adduct having the structure of the following Formula:

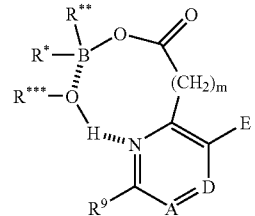

wherein B is boron, O is oxygen
wherein R* and R** are the same and are members selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted phenyl, and substituted or unsubstituted heterocycle,
and wherein A is CH, $CR^{10}$ or N,
and wherein D is N, CH, or $CR^{12}$,
and wherein E is H, OH, alkoxy or 2-(morpholino)ethoxy, $CO_2H$ or $CO_2alkyl$
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2alkyl$, $CONH_2$, OH, alkoxy, aryloxy, SH, S-alkyl, S-aryl, $SO_2alkyl$, $SO_2N(alkyl)_2$, $SO_2NHalkyl$, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NHalkyl$, $CH_2N(alkyl)_2$, halogen, CHO, CH=NOH, $CO_2H$, $CO_2$-alkyl, S-alkyl, $SO_2alkyl$, S-aryl, $SO_2N(alkyl)_2$, $SO_2NHalkyl$, $SO_2NH_2$, $NH_2$, alkoxy, $CF_3$, $SCF_3$, $NO_2$, $SO_3H$ and OH,
and wherein R*** is H or alkyl
and salts of said chemical compound having a structure of said Formula.

49. A compound having the structure which is a member selected from:

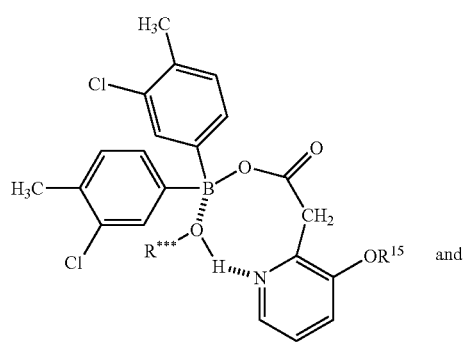

and

-continued

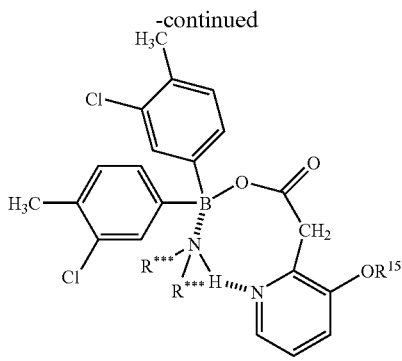

in which
- each R*** is a member independently selected from H and alkyl; and
- $R^{15}$ is a member selected from H and a pharmaceutically compatible counterion.

50. A compound which is a member selected from:
a chemical compound having the structure of the following Formula:

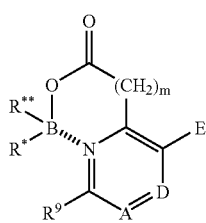

wherein B is boron, O is oxygen
wherein R* and R** are members selected from substituted or unsubstituted phenyl, with the proviso that R* and R** are not both unsubstituted phenyl,
and wherein A is CH, $CR^{10}$ or N,
and wherein D is N, CH, or $CR^{12}$,
and wherein E is H, OH, alkoxy or 2-(morpholino)ethoxy, $CO_2H$ or $CO_2$alkyl
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ and $R^{10}$ are members independently selected from the group consisting of hydrogen, alkyl, cycloalkyl, $(CH_2)_nOH$ (n=1 to 3), $CH_2NH_2$, $CH_2NH$alkyl, $CH_2N(alkyl)_2$, halogen, CHO, CH=NOH, $CO_2H$, $CO_2$-alkyl, S-alkyl, $SO_2$alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
and salts of said chemical compound having a structure of said Formula.

51. A compound which is a member selected from:
a chemical compound having the structure of the following Formula:

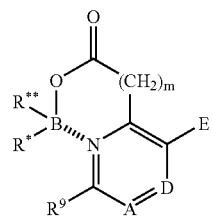

wherein B is boron, O is oxygen
wherein R* and R** are the same and are members selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted phenyl, and substituted or unsubstituted heterocycle,
and wherein A is CH, $CR^{10}$ or N,
and wherein D is N, CH, or $CR^{12}$,
and wherein E is H, OH, alkoxy or 2-(morpholino)ethoxy, $CO_2H$ or $CO_2$alkyl
and wherein m=0-2,
wherein $R^{12}$ is selected from $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2*-amino, 3*-amino, $NH_2SO_2$ and $CONH_2$,
and wherein $R^9$ is a member selected from the group consisting of hydrogen, alkyl, cycloalkyl, $(CH_2)_nOH$ (n=1 to 3), $CH_2NH_2$, $CH_2NH$alkyl, $CFJ2N(alkyl)_2$, halogen, CHO, CH=NOH, $CO_2H$, $CO_2$-alkyl, S-alkyl, $SO_2$, alkyl, S-aryl, $SO_2N(alkyl)_2$, $SO_2NH$alkyl, $SO_2NH_2$, $NH_2$, alkoxy, $CF_3$, $SCF_3$, $NO_2$, $SO_3H$ and OH,
$R^{10}$ is selected from alkyl (greater than $C_4$), $(CH_2)kOH$ (n=1, 2 or 3), $CH_2NH_2$, $CH_2NH$alkyl, $CH_2N(alkyl)_2$, CHO, CH=NOH, $CO_2H$, $CO_2$-alkyl, S-alkyl, $SO_2$-alkyl, S-aryl, alkoxy (greater than $C_4$), $SCF_3$ and $NO_2$
and salts of said chemical compound having a structure of said Formula.

52. The compound of claim 51 wherein said phenyl has the structure

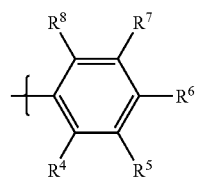

wherein $R^4$, $R^5$, $R^6$, $R^7$ and $R^8$ are each independently selected from the group consisting of hydrogen, alkyl, cycloalkyl, aryl, substituted aryl, aralkyl, substituted aralkyl, $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, $CONH$alkyl, $CON(alkyl)_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2°-amino, 3°-amino, $NH_2SO_2$, $OCH_2CH_2NH_2$, $OCH2CH_2NH$alkyl, $OCH_2CH_2N(alkyl)_2$, oxazolidin-2-yl, or alkyl substituted oxazolidin-2-yl, with the proviso that $R^4$, $R^5$, $R^6$, $R^7$ and $R^8$ are not all hydrogen.

* * * * *